(12) United States Patent
Bokvist et al.

(10) Patent No.: US 9,474,780 B2
(45) Date of Patent: Oct. 25, 2016

(54) GIP AND GLP-1 CO-AGONIST COMPOUNDS

(71) Applicant: Eli Lilly and Company, Indianapolis, IN (US)

(72) Inventors: Bengt Krister Bokvist, Carmel, IN (US); Tamer Coskun, Indianapolis, IN (US); Robert Chadwick Cummins, Carmel, IN (US); Jorge Alsina-Fernandez, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/987,791

(22) Filed: Jan. 5, 2016

(65) Prior Publication Data
US 2016/0199438 A1    Jul. 14, 2016

Related U.S. Application Data

(60) Provisional application No. 62/101,488, filed on Jan. 9, 2015.

(51) Int. Cl.
| C07K 14/405 | (2006.01) |
| A61K 38/16 | (2006.01) |
| C07K 14/00 | (2006.01) |
| A61K 45/06 | (2006.01) |
| C07K 14/605 | (2006.01) |

(52) U.S. Cl.
CPC ............... A61K 38/16 (2013.01); A61K 45/06 (2013.01); C07K 14/001 (2013.01); C07K 14/605 (2013.01)

(58) Field of Classification Search
None
See application file for complete search history.

(56) References Cited

U.S. PATENT DOCUMENTS

| 8,541,368 B2 | 9/2013 | Lau et al. |
| 2015/0299281 A1* | 10/2015 | Just ...................... C07K 14/605 514/7.2 |

FOREIGN PATENT DOCUMENTS

| WO | 2010029159 A1 | 3/2010 |
| WO | 2010071807 A1 | 6/2010 |
| WO | 2011094337 A1 | 8/2011 |
| WO | 2012088116 A1 | 6/2012 |
| WO | 2012088379 A2 | 6/2012 |
| WO | 2012138941 A1 | 10/2012 |
| WO | 2012167744 A1 | 12/2012 |
| WO | 2012171994 A1 | 12/2012 |
| WO | 2013164483 A1 | 7/2013 |
| WO | 2013192129 A1 | 12/2013 |
| WO | 2014060512 A1 | 4/2014 |
| WO | 2014096148 A1 | 6/2014 |

OTHER PUBLICATIONS

Green B D et al: "Structurally Modified Analogues of Glucagon-Like Peptide-1 (GLP-1) and Glucose-Dependent Insulinotropic Polypeptide (GIP) as Futureantidiabetic agents", Current Pharmaceutical Design, Bentham Science Publishers, NL, vol. 10, No. 29, Jan. 1, 2004 (Jan. 1, 2004), pp. 3651-3662, XP009068381,ISSN: 1381-6128, DOI:10.2174/1381612043382774.

* cited by examiner

*Primary Examiner* — Christina Bradley
(74) *Attorney, Agent, or Firm* — Alejandro Martinez

(57) ABSTRACT

The present invention relates to dual incretin peptide mimetic compounds that agonize receptors for both human glucose-dependent insulinotropic polypeptide (GIP) and glucagon-like peptide-1 (GLP-1), and may be useful for treating type 2 diabetes mellitus (T2D).

18 Claims, No Drawings

GIP AND GLP-1 CO-AGONIST COMPOUNDS

The present invention relates to the field of medicine. More particularly, the present invention relates to dual incretin peptide mimetic compounds that agonize receptors for both human glucose-dependent insulinotropic polypeptide (GIP) and glucagon-like peptide-1 (GLP-1), and may be useful for treating type 2 diabetes mellitus (T2D).

T2D is the most common form of diabetes accounting for approximately 90% of all diabetes. T2D is characterized by high blood glucose levels caused by insulin-resistance. The current standard of care for T2D includes diet and exercise along with available oral and injectable glucose lowering drugs. Nonetheless, many patients with T2D still remain inadequately controlled. Currently marketed incretin mimetics or dipeptidyl peptidase IV (DPP-IV) inhibitors only utilize a single established mechanism of action for glycemic control. A compound for T2D is needed that utilizes a dual mechanism of action.

GIP is a 42-amino acid gastrointestinal regulatory peptide that plays a physiological role in glucose homeostasis by stimulating insulin secretion from pancreatic beta cells in the presence of glucose and protecting pancreatic beta cells. GLP-1 is a 37-amino acid peptide that stimulates insulin secretion, protects pancreatic beta cells, and inhibits glucagon secretion, gastric emptying and food intake which leads to weight loss. GIP and GLP-1 are known as incretins; incretin receptor signaling exerts physiologically relevant action critical for glucose homeostasis. In normal physiology, GIP and GLP-1 are secreted from the gut following a meal, and these incretins enhance the physiological response to food including sensation of satiety, insulin secretion, and nutrient disposal. T2D patients have impaired incretin responses.

Dosing of GLP-1 analogues has been found to be limited by adverse effects, such as nausea and vomiting, and as a consequence dosing most often cannot reach full efficacy for glycemic control and weight loss. GIP alone has very modest glucose-lowering ability in type 2 diabetic humans. Both native GIP and GLP-1 are inactivated rapidly by the ubiquitous protease, DPP IV, and therefore, can only be used for short-term metabolic control.

Glucagon is a 29-amino acid peptide produced by the pancreas, and when bound to glucagon receptor, signals the liver to release glucose leading to an increase in blood glucose. GLP-2, a peptide that like GLP-1 is produced from processing of proglucagon, is known to be associated with cellular proliferation in the gut. Thus, stimulation of glucagon and GLP-2 receptors should be minimized during chronic treatment of T2D patients in order to maximize glucose lowering and reduce potential long term carcinogenic risks.

Certain GIP analogs have been described as exhibiting both GIP and GLP-1 activity in WO 2013/164483, WO 2014/192284, and WO 2011/119657.

DPP IV is in the exopeptidase class of proteolytic enzymes. The introduction of non-natural amino acids in a sequence can increase the proteolytic stability of any given peptide. While use of non-natural amino acids can help with the stability of peptides against DPP IV proteolysis and other forms of degradation, it was discovered by Applicants as part of the present invention that non-natural amino acids can have unexpected effects on the balance of agonist activity between GIP and GLP-1. Non-natural amino acids also increase the likelihood that a peptide may be seen as foreign and set off undesirable immune reactions, such as human immunogenicity and injection site reactions.

Fatty acids, through their albumin binding motifs, can improve the pharmacokinetics of a peptide by extending the half-life, for example. While use of fatty acids can improve peptide half-life, it was discovered by Applicants as part of the present invention that the length, composition, and placement of the fatty acid chain and the linker between the peptide and the fatty acid chain can have unexpected effects on the balancing of the GIP and GLP-1 agonist activity.

Tolerability of certain GLP-1 analogues has been found to prevent a dose of the GLP-1 analogue that reaches better efficacy for glycemic control and weight loss. The most common side effects assigned to GLP-1 analogues are nausea and vomiting but some compounds may also impact heart rate. The HPA axis is part of a physiological stress response and GLP-1 has been found to stimulate the HPA axis in rats resulting in increased corticosterone levels providing a potential link to adverse events such as increased heart rate. As part of the present invention, Applicants unexpectedly found that a compound of the present invention did not lead to elevated corticosterone levels like seen with semaglutide in a rat model and so possibly can be dosed to higher efficacy levels than GLP-1R-selective agents.

There remains a need to provide a compound that is a balanced co-agonist of GIP and GLP-1 receptors, but is selective against related glucagon and GLP-2 receptors. Also, there remains a need to provide a compound with balanced co-agonist activity of GIP and GLP-1 receptors which may provide weight loss given activity found in animal models. Additionally, there remains a need to provide a compound with balanced co-agonist activity of GIP and GLP-1 receptors that delivers adequate stability against DPP IV and other forms of degradation, but while still maintaining a low immunogenicity potential. Also, there remains a need to provide a compound with balanced co-agonist activity of GIP and GLP-1 receptors that supports potential once-weekly dosing in humans.

Accordingly, certain compounds of the present invention have lower potential for immunogenicity and injection site reactions than certain GIP-GLP-1 co-agonist compounds in the art. Certain compounds of the present invention have potential for producing weight loss in patients based on animal energy expenditure data. Furthermore, certain compounds of the present invention have a balanced co-agonist activity against GIP and GLP-1 receptors and selectivity against both glucagon and GLP-2 receptors, low immunogenicity potential, and pharmacokinetic (PK) characteristics that support once-weekly dosing in humans. Accordingly, an embodiment of the present invention provides a compound of Formula I:

YX$_1$EGTFTSDYSIX$_2$LDKIAQKAX$_3$VQWLIAGGPSSGAPPPS;

wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H wherein a is 1 to 2 and b is 10 to 20; X$_3$ is Phe or 1-Nal; and the C-terminal amino acid is optionally amidated as a C-terminal primary amide (SEQ ID NO: 11), or a pharmaceutically acceptable salt thereof.

In a further embodiment, the present invention provides a compound of Formula I, wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H wherein a is 1 to 2 and b is 10 to 18; X$_3$ is Phe; and the C-terminal amino acid is optionally amidated as a C-terminal primary amide, or a pharmaceutically acceptable salt thereof.

In a further embodiment, the present invention provides a compound of Formula I, wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H wherein a is 1 to 2 and b is 10 to 18; X$_3$ is 1-Nal; and the C-terminal amino acid is optionally amidated as a C-terminal primary amide, or a pharmaceutically acceptable salt thereof.

In a further embodiment, the present invention provides a compound of Formula I, wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H wherein a is 1 to 2 and b is 14 to 18; X$_3$ is Phe or 1-Nal; and the C-terminal amino acid is optionally amidated as a C-terminal primary amide, or a pharmaceutically acceptable salt thereof. In a further embodiment, the present invention provides a compound wherein b is 16 to 18. Additionally, the present invention provides a compound wherein b is 18.

In a further embodiment, the present invention provides a compound of Formula I, wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H wherein a is 1 and b is 10 to 18; X$_3$ is Phe or 1-Nal; and the C-terminal amino acid is optionally amidated as a C-terminal primary amide, or a pharmaceutically acceptable salt thereof.

In a further embodiment, the present invention provides a compound of Formula I, wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H wherein a is 2 and b is 10 to 18; X$_3$ is Phe or 1-Nal; and the C-terminal amino acid is optionally amidated as a C-terminal primary amide, or a pharmaceutically acceptable salt thereof.

In a further embodiment, the present invention provides a compound of Formula I, wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H wherein a is 1 to 2 and b is 10 to 18; X$_3$ is Phe or 1-Nal; and the C-terminal amino acid is amidated as a C-terminal primary amide, or a pharmaceutically acceptable salt thereof.

In an embodiment, the present invention provides a compound of the Formula:

YX$_1$EGTFTSDYSIX$_2$LDKIAQKAFVQWLIAGGPSSGAPPPS;

wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_1$-CO—(CH$_2$)$_{18}$—CO$_2$H; and the C-terminal amino acid is amidated as a C-terminal primary amide (SEQ ID NO: 3), or a pharmaceutically acceptable salt thereof.

In an embodiment, the present invention provides a compound of the Formula:

YX$_1$EGTFTSDYSIX$_2$LDKIAQKAX$_3$VQWLIAGGPSSGAPPPS;

wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_2$-CO—(CH$_2$)$_{18}$—CO$_2$H; X$_3$ is 1-Nal; and the C-terminal amino acid is amidated as a C-terminal primary amide (SEQ ID NO: 4), or a pharmaceutically acceptable salt thereof.

In an embodiment, the present invention provides a compound of the Formula:

YX$_1$EGTFTSDYSIX$_2$LDKIAQKAFVQWLIAGGPSSGAPPPS;

wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_1$-CO—(CH$_2$)$_{16}$—CO$_2$H; and the C-terminal amino acid is amidated as a C-terminal primary amide (SEQ ID NO: 5), or a pharmaceutically acceptable salt thereof.

In an embodiment, the present invention provides a compound of the Formula:

YX$_1$EGTFTSDYSIX$_2$LDKIAQKAFVQWLIAGGPSSGAPPPS;

wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_2$-CO—(CH$_2$)$_{16}$—CO$_2$H; and the C-terminal amino acid is amidated as a C-terminal primary amide (SEQ ID NO: 6), or a pharmaceutically acceptable salt thereof.

In an embodiment, the present invention provides a compound of the Formula:

YX$_1$EGTFTSDYSIX$_2$LDKIAQKAFVQWLIAGGPSSGAPPPS wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_2$-CO—(CH$_2$)$_{18}$—CO$_2$H; and the C-terminal amino acid is amidated as a C-terminal primary amide (SEQ ID NO: 7), or a pharmaceutically acceptable salt thereof.

In an embodiment, the present invention provides a compound of the Formula:

YX$_1$EGTFTSDYSIX$_2$LDKIAQKAX$_3$VQWLIAGGPSSGAPPPS wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_1$-CO—(CH$_2$)$_{16}$—CO$_2$H; X$_3$ is 1-Nal; and the C-terminal amino acid is amidated as a C-terminal primary amide (SEQ ID NO: 8), or a pharmaceutically acceptable salt thereof.

In an embodiment, the present invention provides a compound of the Formula:

YX₁EGTFTSDYSIX₂LDKIAQKAX₃VQWLIAGGPSSGAPPPS wherein X₁ is Aib; X₂ is Aib; K at position 20 is chemically modified through conjugation to the epsilon-amino group of the K side-chain with ([2-(2-Amino-ethoxy)-ethoxy]-acetyl)₂-(γGlu)₂-CO—(CH₂)₁₆—CO₂H; X₃ is 1-Nal; and the C-terminal amino acid is amidated as a C-terminal primary amide (SEQ ID NO: 9), or a pharmaceutically acceptable salt thereof.

In an embodiment, the present invention provides a compound of the Formula:

YX₁EGTFTSDYSIX₂LDKIAQKAX₃VQWLIAGGPSSGAPPPS wherein X₁ is Aib; X₂ is Aib; K at position 20 is chemically modified through conjugation to the epsilon-amino group of the K side-chain with ([2-(2-Amino-ethoxy)-ethoxy]-acetyl)₂-(γGlu)₁-CO—(CH₂)₁₈—CO₂H; X₃ is 1-Nal; and the C-terminal amino acid is amidated as a C-terminal primary amide (SEQ ID NO: 10), or a pharmaceutically acceptable salt thereof.

In an embodiment, the present invention provides a composition comprising a compound of the present invention with a pharmaceutically acceptable carrier, diluent, or excipient.

In an embodiment, the present invention provides a method of treating type 2 diabetes mellitus, comprising administering to a patient in need thereof, an effective amount of a compound of the present invention. In a further embodiment, the present invention provides a method of treating type 2 diabetes mellitus further comprising administering simultaneously, separately, or sequentially in combination with an effective amount of one or more agents selected from metformin, thiazolidinediones, sulfonylureas, dipeptidyl peptidase 4 inhibitors, and sodium glucose co-transporters.

In an embodiment, the present invention provides a method to improve glycemic control in adults with type 2 diabetes mellitus, comprising administering to a patient in need thereof, an effective amount of a compound of the present invention as an adjunct to diet and exercise. In an embodiment, the present invention provides a method for chronic weight management in adults with an initial body mass index ≥27 and type 2 diabetes mellitus, comprising administering to a patient in need thereof, an effective amount of a compound of the present invention as an adjunct to a reduced-calorie diet and increased physical activity.

In an embodiment, the present invention provides a method to treat metabolic syndrome, comprising administering to a patient in need thereof, an effective amount of a compound of the present invention. In a further embodiment, the present invention provides a method to treat dyslipidemia, obesity, and/or hepatic steatosis associated with insulin resistance and diabetes, comprising administering to a patient in need thereof, an effective amount of a compound of the present invention. Additionally, the present invention provides a method to treat frailty or increase bone strength, comprising administering to a patient in need thereof, an effective amount of a compound of the present invention.

In an embodiment, the present invention provides a compound of the present invention for use in therapy. In a further embodiment, the present invention provides a compound of the present invention for use in the treatment of type 2 diabetes mellitus. In a further embodiment, the present invention provides a compound of the present invention in simultaneous, separate, or sequential combination with one or more agents selected from metformin, thiazolidinediones, sulfonylureas, dipeptidyl peptidase 4 inhibitors, and sodium glucose co-transporters for use in the treatment of type 2 diabetes mellitus.

In an embodiment, the present invention provides a compound of the present invention for use in glycemic control in adults with type 2 diabetes mellitus as an adjunct to diet and exercise. In an embodiment, the present invention provides a compound of the present invention for use in chronic weight management in adults with an initial body mass index ≥27 and type 2 diabetes mellitus as an adjunct to a reduced-calorie diet and increased physical activity.

In an embodiment, the present invention provides the use of a compound of the present invention for the manufacture of a medicament for the treatment of type 2 diabetes mellitus. In a further embodiment, the present invention provides the use of a compound of the present invention in simultaneous, separate, or sequential combination with one or more agents selected from metformin, thiazolidinediones, sulfonylureas, dipeptidyl peptidase 4 inhibitors, and sodium glucose co-transporters for the manufacture of a medicament for the treatment of type 2 diabetes mellitus.

The present invention provides compounds that display a balanced GIP and GLP-1 activity. Balanced activity against GIP and GLP-1 as used herein refers to a compound that has affinity for GIP receptors and GLP-1 receptors in an in vitro binding assay at a molar ratio that is close to 1:1, such as 1:1 GLP-1/GIP, 2:1 GLP-1/GIP, 3:2 GLP-1/GIP, 1:2 GLP-1/GIP, or 2:3 GLP-1/GIP.

The present invention provides compounds that display selectivity for GIP and GLP-1 receptors versus receptors for glucagon and GLP-2. The term "selectivity" or "selective against" when used herein to reference GIP and GLP-1 activity in comparison to glucagon activity, refers to a compound that displays 1000-, 500-, or about 100-fold higher potency for GIP and GLP-1 over glucagon when the data is normalized from the respective in vitro binding assays. The term "selectivity" or "selective against" when used herein to reference GIP and GLP-1 activity in comparison to GLP-2 activity, refers to a compound that displays 250-, 200-, 100-, or about 50-fold higher potency for GIP and GLP-1 over GLP-2 when the data is normalized from the respective in vitro functional assays.

The present invention provides a method for treatment of type 2 diabetes in a patient comprising administering to a patient in need of such treatment an effective amount of a compound of the present invention, or a pharmaceutically acceptable salt thereof. The present invention also provides a method for treatment of type 2 diabetes in a patient comprising administering to a patient in need of such treatment an effective amount of a compound of the present invention, or a pharmaceutically acceptable salt thereof, wherein the administration is subcutaneous. The present invention also provides a method of treatment of type 2 diabetes in a patient comprising administering to a patient in need of such treatment an effective amount of a compound of the present invention, or a pharmaceutically acceptable salt thereof, and simultaneously, separately, or sequentially an effective amount of one or more other active ingredients. In one embodiment, the other active ingredient or ingredients is currently available oral glucose lowering drugs from a class of drugs that is considered prior to administration the standard of care as determined by industry guidelines such as the American Diabetes Association.

The compounds of the present invention utilize a fatty acid chemically conjugated to the epsilon-amino group of a lysine side-chain. The fatty acid is conjugated to the epsilon-amino group of a lysine side-chain through a linker. The linker comprises [2-(2-Amino-ethoxy)-ethoxy]-acetyl)$_2$-($\gamma$Glu)$_a$ wherein a is 1 to 2. The fatty acid and the gamma-glutamic acid in the linker act as albumin binders, and provide the potential to generate long-acting compounds. Compounds of the present invention comprise a lysine at position 20 that is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H wherein a is 1 to 2 and b is 10 to 20. As shown in the chemical structures of Examples 1 and 2, the first unit of [2-(2-Amino-ethoxy)-ethoxy]-acetyl is linked to the epsilon-amino group of the lysine side-chain. The second unit of [2-(2-Amino-ethoxy)-ethoxy]-acetyl is then attached to the amino-group of the first unit of [2-(2-Amino-ethoxy)-ethoxy]-acetyl. Then, the first unit of $\gamma$Glu is attached to the amino-group of the second unit of [2-(2-Amino-ethoxy)-ethoxy]-acetyl through the $\gamma$-carboxyl group of the side-chain. When a=2, the second unit of $\gamma$Glu is attached to the $\alpha$-amino-group of the first unit of $\gamma$Glu through the $\gamma$-carboxyl group of the side-chain. Finally, the symmetrical fatty acid is attached to the $\alpha$-amino-group of the first (when a=1) or second (when a =2) unit of $\gamma$Glu.

The compounds of the invention are preferably formulated as pharmaceutical compositions administered by parenteral routes (e.g., subcutaneous, intravenous, intraperitoneal, intramuscular, or transdermal). Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006). The preferred route of administration is subcutaneous.

The compounds of the present invention may react with any of a number of inorganic and organic acids to form pharmaceutically acceptable acid addition salts.

Pharmaceutically acceptable salts and common methodology for preparing them are well known in the art. See, e.g., P. Stahl, et al. Handbook of Pharmaceutical Salts: Properties, Selection and Use, 2nd Revised Edition (Wiley-VCH, 2011); S. M. Berge, et al., "Pharmaceutical Salts," Journal of Pharmaceutical Sciences, Vol. 66, No. 1, January 1977. Pharmaceutically acceptable salts of the present invention include trifluoroacetate, hydrochloride, and acetate salts.

As used herein, the term "effective amount" refers to the amount or dose of compound of the present invention, or a pharmaceutically acceptable salt thereof which, upon single or multiple dose administration to the patient, provides the desired effect in the patient under diagnosis or treatment. An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

As used herein, the term "treating" or "to treat" includes restraining, slowing, stopping, or reversing the progression or severity of an existing symptom or disorder.

As used herein, "semaglutide" refers to a chemically synthesized GLP-1 analogue that has the peptide backbone and overall compound structure of that found in CAS Registry Number 910463-68-2.

Certain compounds of the present invention are generally effective over a wide dosage range. For example, dosages for once-weekly dosing may fall within the range of about 0.05 to about 30 mg per person per week. Certain compounds of the present invention may be dosed daily. Additionally, certain compounds of the present invention may be dosed once-weekly.

The amino acid sequences of the present invention contain the standard single letter or three letter codes for the twenty naturally occurring amino acids. Additionally, "Aib" is alpha amino isobutyric acid, and "1-Nal" is 1-Naphthylalanine.

The present invention also encompasses novel intermediates and processes useful for the synthesis of compounds of the present invention, or a pharmaceutically acceptable salt thereof. The intermediates and compounds of the present invention may be prepared by a variety of procedures known in the art. In particular, the process using chemical synthesis is illustrated in the Examples below. The specific synthetic steps for each of the routes described may be combined in different ways to prepare compounds of the present invention, or salts thereof. The reagents and starting materials are readily available to one of ordinary skill in the art. It is understood that these Examples are not intended to be limiting to the scope of the invention in any way.

EXAMPLE 1

YX$_1$EGTFTSDYSIX$_2$LDKIAQKAFVQWLIAGGPSSGAPPPS wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-($\gamma$Glu)$_1$-CO—(CH$_2$)$_{18}$—CO$_2$H; and the C-terminal amino acid is amidated as a C-terminal primary amide (SEQ ID NO: 3)

Trifluoroacetate Salt

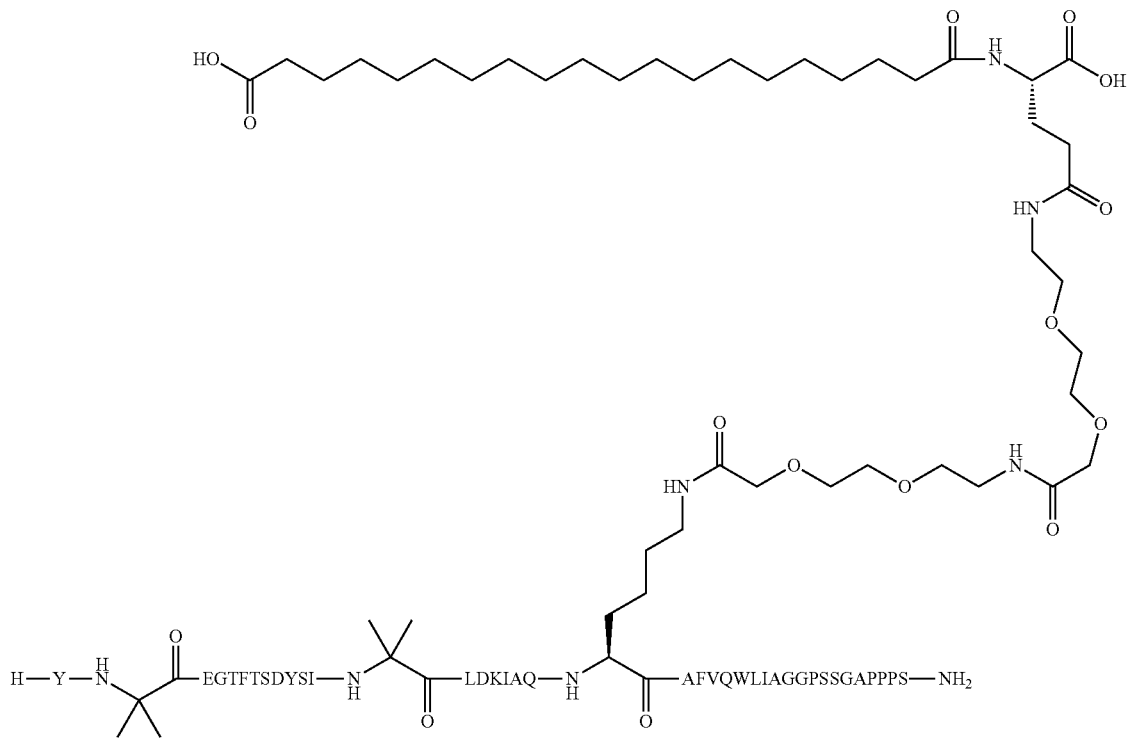

The above structure contains the standard single letter amino acid code with exception of residues Aib2, Aib13 and K20 where the structures of these amino acid residues have been expanded.

The peptide according to SEQ ID NO: 3 of the present invention is generated by solid-phase peptide synthesis using a Fmoc/t-Bu strategy carried out on a Symphony automated peptide synthesizer (PTI Protein Technologies Inc.) starting from RAPP AM-Rink Amide resin and with couplings using 6 equivalents of amino acid activated with diisopropylcarbodiimide (DIC) and hydroxybenzotriazole (HOBt) (1:1:1 molar ratio) in dimethylformamide (DMF) for 90 min at 25° C.

Extended couplings (4h each) for Pro31, Trp25, Gln24, Val23, Phe22, Lys20, Gly4, Glu3 and Aib2 are necessary to improve the quality of the crude peptide. A Fmoc-Lys (Alloc)-OH building block is used for Lys20 coupling (orthogonal protecting group) to allow for site specific attachment of the fatty acid moiety later on in the synthetic process. The following conditions are used for the coupling of Fmoc-Ile-OH at position 12: Fmoc-Ile-OH (6 equiv), PyBOP (6 equiv), and DIEA (12 equiv) in DMF for 24 h at 25° C. The N-terminal residue is incorporated as Boc-Tyr (tBu)-OH using DIC-HOBt protocols as described above.

After finishing the elongation of the peptide-resin described above, the Alloc protecting group present in Lys20 is removed using catalytic amounts of Pd(PPh$_3$)$_4$ in the presence of PhSiH$_3$ as a scavenger. Additional coupling/deprotection cycles using a Fmoc/t-Bu strategy to extend the Lys20 side-chain involved Fmoc-NH-PEG$_2$-CH$_2$COOH (ChemPep Catalog#280102), Fmoc-Glu(OH)-OtBu (ChemPep Catalog#100703) and HOOC—(CH$_2$)$_{18}$—COOtBu. In all couplings, 3 equivalents of the building block are used with PyBOP (3 equiv) and DIEA (6 equiv) in DMF for 4h at 25° C.

Concomitant cleavage from the resin and side chain protecting group removal are carried out in a solution containing trifluoroacetic acid (TFA): triisopropylsilane: 1,2-ethanedithiol: water: thioanisole 90:4:2:2:2 (v/v) for 2 h at 25° C. followed by precipitation with cold ether. Crude peptide is purified to >99% purity (15-20% purified yield) by reversed-phase HPLC chromatography with water/acetonitrile (containing 0.05% v/v TFA) gradient on a C18 column, where suitable fractions are pooled and lyophilized.

In a synthesis performed essentially as described above, the purity of Example 1 was examined by analytical reversed-phase HPLC, and identity was confirmed using LC/MS (observed: M+3H$^+$/3=1605.2; Calculated M+3H$^+$/3=1605.5; observed: M+4H$^+$/4=1204.3; Calculated M+4H$^+$/4=1204.4).

EXAMPLE 2

YX$_1$EGTFTSDYSIX$_2$LDKIAQKAX$_3$VQWLIAGGPSSGAPPPS wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_2$-CO—(CH$_2$)$_{18}$—CO$_2$H; X$_3$ is 1-Nal; and the C-terminal amino acid is amidated as a C-terminal primary amide (SEQ ID NO: 4)

Trifluoroacetate Salt

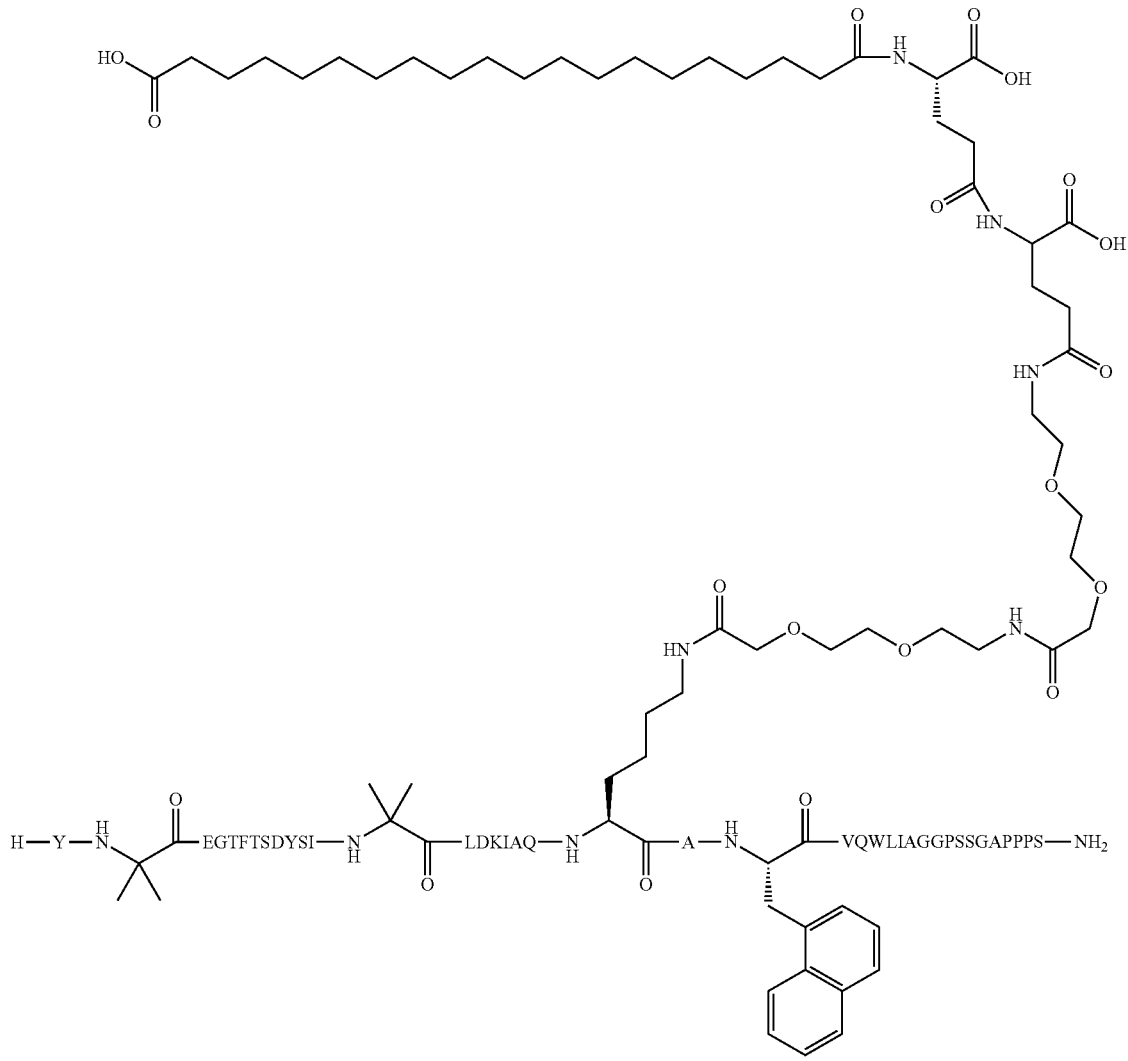

The above structure contains the standard single letter amino acid code with exception of residues Aib2, Aib13, $K_{20}$ and 1-Nal22 where the structures of these amino acid residues have been expanded.

The peptide according to SEQ ID NO: 4 of the present invention is synthesized similarly as described above in Example 1. The following conditions are used for the coupling of Fmoc-1Nal-OH at position 22: Fmoc-1Nal-OH (6 equiv), PyBOP (6 equiv), and DIEA (12 equiv) in DMF for 4 h at 25° C.

EXAMPLE 3

YX₁EGTFTSDYSIX₂LDKIAQKAFVQWLIAGGPSSGAPPPS wherein $X_1$ is Aib; $X_2$ is Aib; K at position 20 is chemically modified through conjugation to the epsilon-amino group of the K side-chain with ([2-(2-Amino-ethoxy)-ethoxy]-acetyl)$_2$-($\gamma$Glu)$_1$-CO—(CH$_2$)$_{16}$—CO$_2$H; and the C-terminal amino acid is amidated as a C-terminal primary amide (SEQ ID NO: 5)

Trifluoroacetate Salt

The compound according to SEQ ID NO: 5 of the present invention is synthesized similarly as described above for Example 1.

EXAMPLE 4

YX₁EGTFTSDYSIX₂LDKIAQKAFVQWLIAGGPSSGAPPPS wherein $X_1$ is Aib; $X_2$ is Aib; K at position 20 is chemically modified through conjugation to the epsilon-amino group of the K side-chain with ([2-(2-Amino-ethoxy)-ethoxy]-acetyl)$_2$-($\gamma$Glu)$_2$-CO—(CH$_2$)$_{16}$—CO$_2$H; and the C-terminal amino acid is amidated as a C-terminal primary amide (SEQ ID NO: 6)

Trifluoroacetate Salt

The compound according to SEQ ID NO: 6 of the present invention is synthesized similarly as described above for Example 1.

EXAMPLE 5

YX$_1$EGTFTSDYSIX$_2$LDKIAQKAFVQWLIAGGPSSGAPPPS wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_2$-CO—(CH$_2$)$_{18}$—CO$_2$H; and the C-terminal amino acid is amidated as a C-terminal primary amide (SEQ ID NO: 7)

Trifluoroacetate Salt

The compound according to SEQ ID NO: 7 of the present invention is synthesized similarly as described above for Example 1.

EXAMPLE 6

YX$_1$EGTFTSDYSIX$_2$LDKIAQKAX$_3$VQWLIAGGPSSGAPPPS wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_1$-CO—(CH$_2$)$_{16}$—CO$_2$H; X$_3$ is 1-Nal; and the C-terminal amino acid is amidated as a C-terminal primary amide (SEQ ID NO: 8)

Trifluoroacetate Salt

The compound according to SEQ ID NO: 8 of the present invention is synthesized similarly as described above for Example 1.

EXAMPLE 7

YX$_1$EGTFTSDYSIX$_2$LDKIAQKAX$_3$VQWLIAGGPSSGAPPPS wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_2$-CO—(CH$_2$)$_{16}$—CO$_2$H; X$_3$ is 1-Nal; and the C-terminal amino acid is amidated as a C-terminal primary amide (SEQ ID NO: 9)

Trifluoroacetate Salt

The compound according to SEQ ID NO: 9 of the present invention is synthesized similarly as described above for Example 1.

EXAMPLE 8

YX$_1$EGTFTSDYSIX$_2$LDKIAQKAX$_3$VQWLIAGGPSSGAPPPS wherein X$_1$ is Aib; X$_2$ is Aib; K at position 20 is chemically modified through conjugation to the epsilon-amino group of the K side-chain with ([2-(2-Amino-ethoxy)-ethoxy]-acetyl)$_2$-(γGlu)$_1$-CO—(CH$_2$)$_{18}$—CO$_2$H; X$_3$ is 1-Nal; and the C-terminal amino acid is amidated as a C-terminal primary amide (SEQ ID NO: 10)

Trifluoroacetate Salt

The compound according to SEQ ID NO: 10 of the present invention is synthesized similarly as described above for Example 1.

Assays

Provided below are the conditions and data for Examples in several assays: in vitro function and selectivity, immunogenicity profiling, pharmacokinetics, and in vivo type 2 diabetes models.

In Vitro Function and Selectivity

In Vitro Binding Potency to Human GLP-1 and GIP Receptors

The in vitro binding potency of compounds of the present invention to human GIP and GLP-1 receptors is evaluated by measuring the binding affinities, as K$_i$, using crude cellular membranes obtained from clonal cell lines over-expressing either the human GLP1R cDNA or human GIP-R cDNA.

The human glucose-dependent insulinotropic polypeptide receptor binding assay uses hGIP-R (Usdin, T. B., Gruber, C., Modi, W. and Bonner, T. I., GenBank: AAA84418.1) cloned into pcDNA3.1 (Promega)-NeoR plasmid. The hGIP-R-pcDNA3.1/Neo plasmid is transfected into Chinese Hamster Ovary cells, CHO-S, for suspension cultures and selected in the presence of 500 µg/mL Geneticin (Invitrogen).

Crude plasma membranes are prepared using cells from suspension culture. The cells are lysed on ice in hypotonic buffer containing 25 mM Tris HCl, pH 7.5, 1 mM MgCl$_2$, DNAse1, 20 µ/mL, and Roche Complete™ Inhibitors without EDTA. The cell suspension is homogenized with a glass dounce homogenizer using a Teflon® pestle for 25 strokes. The homogenate is centrifuged at 4° C. at 1800×g for 15 minutes. The supernatant is collected and the pellet resuspended in hypotonic buffer and re-homogenized. The mixture is centrifuged at 1800×g for 15 minutes. The second supernatant is combined with the first supernatant. The combined supernatants are re-centrifuged at 1800×g for 15 minutes to clarify. The clarified supernatant is transferred to high speed tubes and centrifuged at 25,000×g for 30 minutes at 4° C. The membrane pellet is resuspended in homogenization buffer and stored as frozen aliquots at −80° C. freezer until use.

GIP is radioiodinated by the I-125-lactoperoxidase procedure (Markalonis, J. J., Biochem. J. 113:299 (1969)) and purified by reversed phase HPLC (Perkin-Elmer Life and Analytical Sciences NEX-402). The specific activity is 2200 Ci/mmol K$_D$ determination is performed by homologous competition using cold hGIP instead of saturation binding. The receptor binding assay is carried out using a Scintillation Proximity Assay (SPA) with wheat germ agglutinin (WGA) beads (Perkin Elmer Life and Analytical Sciences) previously blocked with 1% fatty acid free BSA (Gibco, 7.5% BSA). The binding buffer contains 25 mM HEPES, pH 7.4, 2.5 mM $CaCl_2$, 1 mM $MgCl_2$, 0.1% fatty acid free BSA, 0.003% Tween20, and Roche Complete™ Inhibitors without EDTA. hGIP and the compounds of the present invention are dissolved in 100% DMSO and stored at −20° C. The compounds are serially diluted into binding buffer. Next, 10 µL diluted compound or 100% DMSO is transferred into Corning® 3632 clear bottom assay plates containing 40 µL assay binding buffer or cold GIP (NSB at 0.1 µM final). Then, 90 µL membranes (3 µg/well), 50 µL [$I^{125}$] GIP (Perkin Elmer Life and Analytical Sciences at 0.15 nM final in reaction), and 50 µL of WGA beads (150 µg/well) is added, sealed, and mixed on a plate shaker for 1 minute. Plates are read with a MicroBeta® scintillation counter after 12 hours of settling time at room temperature.

Results are calculated as a percentage of specific I-125-GIP binding in the presence of compound. The Absolute $IC_{50}$ concentration is derived by non-linear regression of percent specific binding of I-125-GIP versus the concentration of compound added. The $IC_{50}$ concentration is converted to Ki using the Cheng-Prusoff equation.

The GLP-1 receptor binding assay uses cloned human glucagon-like peptide 1 receptor (hGLP-1R) (Graziano M P, Hey P J, Borkowski D, Chicchi G G, Strader C D, *Biochem Biophys Res Commun.* 196(1): 141-6, 1993) isolated from 293HEK membranes. The hGLP-1R cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. *Bio/Technology* 5: 1189-1192, 1987). This plasmid DNA is transfected into 293HEK cells and selected with 200 µg/mL Hygromycin.

Crude plasma membranes are prepared using cells from suspension culture. The cells are lysed on ice in hypotonic buffer containing 25 mM Tris HCl, pH 7.5, 1 mM $MgCl_2$, DNAse1, 20 µ/mL, and Roche Complete™ Inhibitors without EDTA. The cell suspension is homogenized with a glass dounce homogenizer using a Teflon® pestle for 25 strokes. The homogenate is centrifuged at 4° C. at 1800×g for 15 minutes. The supernatant is collected and the pellet resuspended in hypotonic buffer and re-homogenized. The mixture is centrifuged at 1800×g for 15 minutes. The second supernatant is combined with the first supernatant. The combined supernatants are recentrifuged at 1800×g for 15 minutes to clarify. The clarified supernatant is transferred to high speed tubes and centrifuged at 25000×g for 30 minutes at 4° C. The membrane pellet is resuspended in homogenization buffer and stored as frozen aliquots at −80° C. freezer until use.

Glucagon-like peptide 1 (GLP-1) is radioiodinated by the I-125-lactoperoxidase procedure and purified by reversed phase HPLC at Perkin-Elmer Life and Analytical Sciences (NEX308). The specific activity is 2200 Ci/mmol $K_D$ determination is performed by homologous competition instead of saturation binding due to high propanol content in the 1-125 GLP-1 material. The $K_D$ is estimated to be 0.329 nM and is used to calculate Ki values for all compounds tested.

The receptor binding assay is carried out using a Scintillation Proximity Assay (SPA) with wheat germ agglutinin (WGA) beads previously blocked with 1% fatty acid free BSA (Gibco). The binding buffer contains 25 mM HEPES, pH 7.4, 2.5 mM $CaCl_2$, 1 mM $MgCl_2$, 0.1% fatty acid free BSA, 0.003% Tween20, and Roche Complete™ Inhibitors without EDTA. Glucagon-like peptide 1 is dissolved in 100% DMSO at 1 mg/mL and stored frozen at −20° C. in 30 µL aliquots. The glucagon-like peptide 1 aliquot is diluted and used in binding assays within an hour. The peptide analog is dissolved in 100% DMSO and serially diluted in 100% DMSO. Next, 10 µL diluted compounds of the present invention or 100% DMSO are transferred into Corning® 3632 clear bottom assay plates containing 40 µL assay binding buffer or cold glucagon (NSB at 1 µM final). Then, 90 µL membranes (0.5 µg/well), 50 µL 1-125 Glucagon-like peptide 1 (0.15 nM final in reaction), and 50 µL of WGA beads (150 µg/well) is added, sealed, and mixed on a plate shaker for 1 minute. Plates are read with a PerkinElmer Life and Analytical Sciences Trilux MicroBeta® scintillation counter after 12 hours of settling time at room temperature.

Results are calculated as a percentage of specific I-125-Glucagon-like peptide 1 binding in the presence of compounds. The Absolute $IC_{50}$ concentration of compound is derived by non-linear regression of percent specific binding of I-125-Glucagon-like peptide 1 versus the concentration of compound added. The $IC_{50}$ concentration is converted to Ki using the Cheng-Prusoff equation.

In experiments performed essentially as described in this assay, certain compounds of the present invention display an hGLP-1R/hGIPR ratio of approximately 0.5-4.0 (Table 1). The molar binding ratio is normalized to the corresponding molar ratio of a mixture of native GIP and GLP-1. This normalization factor is 4.53 based on binding data for GIP (Ki=0.175 nM) and GLP-1 (Ki=0.793 nM). The value of 1.48 demonstrates the balanced co-agonist activity of Example 1.

TABLE 1

Receptor Binding Affinity, Ki, nM (SEM, n)

| Compound | Human GIP-R | Human GLP-1R | Absolute ratio of hGLP-1R/hGIP-R | Molar ratio of hGLP-1R/hGIP-R |
|---|---|---|---|---|
| Example 1 | 34.4 (5.0, n = 8) | 232 (40, n = 8) | 6.7 | 1.48 |
| GIP, 1-42 | 0.175 (0.022, n = 8) | >175 (n = 14) | >1000 | |
| GLP-1, 7-36-$NH_2$ | >100 (n = 15) | 0.793 (0.099, n = 8) | <0.008 | |
| Example 3 | 26.7 (2.3, n = 17) | 427 (33, n = 17) | 16 | 3.53 |
| Example 6 | 44.2 (3.6, n = 14) | 365 (28, n = 14) | 8.3 | 1.83 |
| Example 7 | 46.1 (5.9, n = 11) | 352 (39, n = 11) | 7.6 | 1.68 |
| Example 8 | 67.5 (9.9, n = 6) | 307 (35, n = 6) | 4.5 | 0.99 |
| Example 4 | 40.7 (5.1, n = 7) | 714 (76, n = 7) | 17.5 | 3.86 |
| Example 2 | 63.9 (11.8, n = 8) | 344 (60, n = 8) | 5.4 | 1.19 |
| Example 5 | 17.8 (3.0, n = 5) | 158 (32, n = 5) | 8.9 | 1.96 |

Means are expressed as geometric means with the standard error of the mean (SEM) and the number of replicates (n) indicated in parenthesis. A qualifier (>) indicates data did not reach 50% inhibition and the $K_i$ is calculated using the highest concentration tested in the assay.

Functional hGIP-R, hGLP-1R, and hGCGR Assays.

The in vitro functional activity towards human GIP, GLP-1, and glucagon receptors for compounds of the present invention are determined in HEK-293 clonal cell lines expressing these receptors. Each receptor over-expressing cell line is treated with compounds of the present invention in DMEM (Gibco Cat#31053) supplemented with 1× GlutaMAX™ (Gibco Cat#35050), 0.25% FBS, 0.05% fraction V BSA, 250 µM IBMX and 20 mM HEPES in a 40 µl assay volume. After an incubation of 60 minutes at room temperature, the resulting increase in intracellular cAMP is quantitatively determined using the CisBio cAMP Dynamic 2 HTRF Assay Kit (Bedford, Mass.). Briefly, cAMP levels within the cell are detected by adding the cAMP-d2 conjugate in cell lysis buffer (20 µl) followed by the antibody anti-cAMP-Eu$^{3+}$-Cryptate, also in cell lysis buffer (20 µl). The resulting competitive assay is incubated for at least 60 minutes at room temperature, then detected using a PerkinElmer Envision® instrument with excitation at 320 nm and emission at 665 nm and 620 nm Envision units (emission at 665 nm/620 nm*10,000) are inversely proportional to the amount of cAMP present and are converted to nM cAMP per well using a cAMP standard curve. The amount of cAMP generated (nM) in each well is converted to a percent of the maximal response observed with either human GIP(1-42)NH$_2$, human GLP-1(7-36)NH$_2$, or human glucagon controls. A relative EC$_{50}$ value and percent top (E$_{max}$) is derived by non-linear regression analysis using the percent maximal response versus the concentration of the compound of the present invention, fitted to a four-parameter logistic equation.

In experiments performed essentially as described in this assay, certain compounds of the present invention demonstrate activity against human GIP and GLP-1 receptors, while also demonstrating selectivity over the glucagon receptor. In Table 2, functional potency against the receptors is shown for the native hGIP(1-42)NH$_2$, hGLP-1(7-36)NH$_2$, and hGlucagon controls, and certain compounds of the present invention.

Functional Activation of hGIP-R Cells to Generate Intracellular cAMP in Incretin-Secreting Cell Lines The functional activity of hGIP-R for compounds of the present invention are demonstrated by the ability of the compounds to generate intracellular cAMP in GLUTag cells, a stable immortalized relatively differentiated murine enteroendocrine cell line that expresses the proglucagon gene and secretes the glucagon-like peptides in a regulated manner. The cells are maintained at 37° C., 5% CO$_2$, 95% humidity in DMEM medium supplemented with 5.5 mM glucose, 10% FBS, and 2 mM glutamine Prior to assay, cells are trypsinized, pelleted, and seeded into 96-well tissue culture assay plates at a density of 20,000 cells/well. Cells are allowed to attach and are incubated for 48 hours at 37° C., 5% CO$_2$. On the day of the assay, media is decanted from cells and 50 µl EBSS Buffer (0.1% BSA, 2 mM glucose and 0.25 mM IBMX) containing a range of compound concentrations (0.001-3 µM) is added to cells. The plate is incubated at 37° C. for one hour and cAMP levels determined using Cisbio Dynamic 2 cAMP HTRF kit (Bedford, Mass.). 25 µl of anti-cAMP cryptate and 25 µl cAMP d2 is added to each well and plates incubated for one hour at room temperature. Plates are read at 620 nm and 665 nm on a Tecan Genios Pro. Results are calculated from the 665 nm/620 nm ratio multiplied by 10000, and converted to nM cAMP per well using a cAMP standard curve. Data is analyzed with GraphPad using a 4-parameter non-linear logistic algorithm In experiments performed essentially as described in this assay, certain compounds of the present invention show a dose-dependent, enhanced cAMP accumulation of GLUTag cells (Table 3). The native GLP-1 control fails to induce any changes in cAMP at all concentrations tested and indicates that this cell system exclusively expresses the GIP receptor;

TABLE 2

Functional Potency (EC$_{50}$) against human GIP, GLP-1, and glucagon receptors.

| | Human GIP-R | | Human GLP-1R | | Human GCGR | |
|---|---|---|---|---|---|---|
| Compound | EC$_{50}$, nM ± SEM (n) | E$_{max}$, % | EC$_{50}$, nM ± SEM (n) | E$_{max}$, % | EC$_{50}$, nM ± SEM, (n) | E$_{max}$, % |
| Example 1 | 11.0 ± 0.9 (17) | 97.9 ± 3.0 | 71.2 ± 7.2 (17) | 85.2 ± 4.4 | >1000 (13) | ND |
| Example 3 | 3.15 ± 0.34 (14) | 106 ± 3 | 33.9 ± 3.2 (14) | 96.2 ± 6.2 | >1000 (10) | ND |
| Example 6 | 4.40 ± 0.71 (13) | 106 ± 3 | 28.4 ± 4.2 (13) | 104 ± 4 | >1000 (9) | ND |
| Example 7 | 8.07 ± 0.70 (17) | 106 ± 3 | 35.5 ± 2.6 (17) | 97.2 ± 3.4 | >1000 (13) | ND |
| Example 8 | 21.1 ± 2.7 (14) | 108 ± 4 | 57.9 ± 6.8 (13) | 88.4 ± 2.3 | >1000 (10) | ND |
| Example 4 | 3.76 ± 0.83 (6) | 102 ± 3 | 66.9 ± 14.9 (6) | 100 ± 5 | >1000 (2) | ND |
| Example 2 | 17.5 ± 2.0 (13) | 94.7 ± 2.0 | 75.7 ± 6.0 (13) | 98.2 ± 5.5 | >1000 (9) | ND |
| Example 5 | 8.76 ± 0.86 (10) | 105 ± 2 | 70.9 ± 9.7 (10) | 105 ± 4 | >1000 (10) | ND |
| hGLP-1(7-36)NH$_2$ | | | 0.176 ± 0.015 (17) | 102 ± 2 | | |
| hGIP(1-42)NH$_2$ | 0.135 ± 0.010 (17) | 100 ± 1 | | | | |
| hGlucagon | | | | | 0.0208 ± 0.0024 (13) | 115 ± 2 |

Means for EC$_{50}$ are expressed as geometric means +/− standard error of the mean (SEM) with the number of replicates (n) indicated in parenthesis.
Means for E$_{max}$ are expressed as the arithmetic mean +/− standard error.
ND signifies that agonist activity was not detected.
A qualifier (>) indicates that an EC$_{50}$ could not be determined.
All values shown are to three significant digits therefore, certain compounds of the present invention can be shown to exert an effect through the GIP receptor.

TABLE 3

EC50 in GLUTag cells.

| Compound | Average EC50, nM (n) |
|---|---|
| Example 3 | 1610 (1) |
| Example 7 | 2746 (1) |
| Example 4 | 2186 (1) |
| Example 2 | 2918 (1) |
| Example 1 | 1494 (2) |
| Native GIP | 11.62 (3) |

Measurement of Intracellular cAMP in HEK293 Cells Transiently Expressing the Human GLP-2 Receptor The functional activity of hGLP-2R in the presence of compounds of the present invention is demonstrated by measuring intracellular cAMP in HEK293 cells. These cells are passaged in complete medium, transfected in suspension with Promega Fugene6 reagent and human full-length GLP-2R cDNA in pcDNA3.1 expression vector, and allowed to adhere to tissue culture flasks in a humidified 37° C. 5% $CO_2$ environment. Following approximately 48 hours of propagation, cells are lifted, strained, and cryopreserved with controlled rate freezing and 10% DMSO as a cryoprotectant. In subsequent assays, a single assay-ready vial from the same cell freeze is thawed to minimize inter-assay variation. On the day of the cellular assay, freezing medium is exchanged with Invitrogen 31053 DMEM containing 0.5% FBS.

Cells are counted for viability and equilibrated for approximately one to two hours at 37° C. prior to treatment. Compounds of the present invention are solubilized in DMSO and immediately diluted in DMEM medium containing 0.1% fraction V BSA and the non-specific phosphodiesterase inhibitor, IBMX. Duration of treatment is 30 minutes at 37° C. Final DMSO concentration does not exceed 1.1%, and final IBMX concentration is 250 µM. Cyclic AMP is measured using the dynamic 2 assay with homogenous time-resolved fluorescence technology (Cisbio Bioassays, Bedford, Mass.). Respective cAMP concentrations are deduced from the ratio method of calculation and external standards. Sigmoidal dose-responses of tested compounds are examined using the four parameter logistic equation and compared to the native $C_{18}$-acylated ligand.

In experiments performed essentially as described in this assay, the $C_{18}$-acylated human GLP-2 control has an $EC_{50}$ value for receptor activation of 1.71 nM while certain compounds of the present invention have $EC_{50}$ values from approximately 100× to 1000× higher. The $EC_{50}$ values for certain compounds of the present invention demonstrate selectivity against the GLP-2 receptor.

TABLE 4

GLP-2R functional activity measurement in HEK293 cells.

| Compound | Rel EC50 (nM) | n |
|---|---|---|
| GLP2-$C_{18}$-diacid | 1.857 | 4 |
| Example 3 | 199.3 | 4 |
| Example 7 | 1,800 | 4 |
| Example 4 | 405 | 2 |
| Example 1 | 238 | 4 |
| Example 2 | 1612 | 2 |

Rodent Islet Insulin Secretion

To assess action of compounds of the present invention in a system representing physiological GLP-1R and GIP-R expression levels insulin secretion, compounds are tested for effects on insulin secretion from wild-type rodent islets.

After common bile duct cannulation in male C57Bl/6 mice (22-26 g) or male Sprague-Dawley rats (approx. 250 g), the pancreas is distended with Hank's buffer (3 ml for mice or 10 ml for rats, containing 2% BSA and 0.75 mg/ml Clzyme collagenase (VitaCyte). Subsequently, tissues are digested in Hank's buffer at 37° C. for 11-13 minutes (mice) or 14-16 minutes for rat pancreas. Purified islets (Histopaque-1100 gradient [Sigma-Aldrich], 18 mM at 750× gravity) are cultured overnight in RPMI-1640 medium (Invitrogen) containing 10% FBS, 100 U/ml penicillin and 100 µg/ml streptomycin, and preconditioned by starvation in Earle's Balanced Salt Solution (EBSS) supplemented with 0.1% BSA and 2.8 mM glucose. Subsequently, islets are incubated in EBSS (Invitrogen) supplemented with 0.1% BSA, 2.8-11.2 mM glucose and increasing levels of compound (6 batches of 4 islets/condition). GLP-1(7-36)amide (30 nM) is used as a positive control. Insulin is measured over 90 minutes in supernatant using the MSD Insulin Assay (Meso Scale, Gaithersburg, Md.).

Certain compounds of the present invention dose-dependently increase insulin secretion from both rat and mouse islets as depicted in Table 5.

TABLE 5

Rodent Islet Insulin Secretion

| Compound | Mean ED50 (nM) | N |
|---|---|---|
| Rat islet insulin secretion | | |
| Example 3 | 34.9 | 2 |
| Example 1 | 15.5 | 3 |
| Mouse islet insulin secretion | | |
| Example 3 | 58.9 | 2 |
| Example 6 | 51.4 | 1 |
| Example 7 | 11.3 | 1 |
| Example 4 | 3.5 | 1 |
| Example 2 | 30.0 | 1 |
| Example 1 | 47.2 | 2 |

Immunogenicity Profiling

The risk of immunogenicity for compounds of the present invention is assessed using in silico prediction programs, such as Epivax in silico analysis. The risk of immunogenicity for compounds of the present invention is also assessed by an ex-vivo method to measure cultured T cells responses ($^3$H-thymidine uptake and IL-2 cytokine secretion) in the presence of compounds of the present invention.

With Epivax immune-informatic tools, an in silico assessment is performed on compounds of the present invention to predict an immune response following administration. The analysis utilizes the probability of a 9-mer frame to bind to a given human leukocyte antigen leukocyte antigen (HLA) allele and then detection of these Epi-Bars. For Example 1, a EpiMatrix score of approximately +1.13 indicates a much lower potential to induce an immune response compared to native GIP peptide backbone with a EpiMatrix score of +15.4. A GIP/GLP-1 co-agonist Example from WO 2011/119657 had a score of +29.5.

A measure of predicted clinical immunogenicity is also examined for compounds of the present invention by using the characterization of CD4+ T-cell proliferation and IL-2 cytokine secretion in a cohort of 50 healthy donors representative of the world HLA allotype population. Certain compounds of the present invention demonstrate a degree of T-cell stimulation and IL-2 secretion following exposure that does not exceed the threshold associated with known or positive immunogenic compounds, indicating a low risk of producing clinical immunogenicity.

Pharmacokinetics

Pharmacokinetics in Cynomolgus Monkeys.

The in vivo pharmacokinetic properties for compounds of the present invention are demonstrated using cynomolgus monkeys. The compounds are administered by a single intravenous or subcutaneous dose (0.2 mg/kg) in 20 mM citrate buffer (pH 7.0) at a volume of 0.21 ml/kg. Blood is collected from each animal at 2, 4, 8, 12, 24, 48, 72, 96, 120, 144, 168, 204, 240, and 312 hours post-dosage. The plasma concentrations of compounds of the present invention are determined by a LC/MS method. Briefly, a compound of the present invention is extracted from 100% Monkey plasma sample (50 µl) diluted with 1×PBS (150 µl) and mixed with N-butanol (400 µl). Three distinct liquid layers are formed with the compound located in the top layer. A volume of 200 µl is transferred to a v-bottom 96-well plate, dried down using heated Nitrogen gas and reconstituted with 100 µl of 30% acetonitrile/0.1% formic acid. 20 µl of the reconstituted sample is injected onto a Supelco Analytical Discovery bio wide C5 3 µm column. The column effluent is directed into a Thermo Q-Exactive mass spectrometer for detection and quantitation.

In experiments performed essentially as described for this assay, Example 1 reached a mean maximum plasma concentration approximately 8 hours post the subcutaneous dose. The mean half-life is 55 hours and the mean clearance is 0.73 mL/hr/kg. The bioavailability is approximately 83%. This data supports the potential of once-weekly dosing for Example 1. Data for other compounds of the present invention are summarized in Table 6.

TABLE 6

Mean Pharmacokinetic Parameters Following a Single Subcutaneous Dose of 0.2 mg/kg to Male Cynomolgus Monkeys

| Compound | Mean $T_{1/2}$(hr) | Mean Tmax (hr) | Mean Cmax (µg/mL) | Mean $AUC_{0-inf}$ (hr*µg/mL) | Mean CL/F (mL/hr/kg) |
|---|---|---|---|---|---|
| Example 3 | 34 | 8 | 3.0 | 153 | 1.3 |
| Example 7 | 31 | 6 | 2.9 | 136 | 1.5 |
| Example 6 | 23 | 4 | 2.2 | 72.3 | 2.8 |
| Example 8 | 23 | 10 | 1.0 | 42.8 | 4.7 |
| Example 2 | 43 | 24 | 2.1 | 173 | 1.2 | n = 2,
$AUC_{0-inf}$ = area under the curve from 0 to infinity,
CL/F = clearance/bioavailability,
Tmax = time to maximum concentration,
Cmax = maximum plasma concentration,
$T_{1/2}$ = half-life.

Dose Potency Projection

The intravenous glucose tolerance test (ivGTT) in the rat is used to estimate relative potency of compounds of the present invention in comparison to semaglutide. Single subcutaneous (SC) doses of 0.1-10 nmol/kg of each compound are administered to the rats and an ivGTT is administered to each rat 16 hours post-dosage. Exposure is measured at the time of the ivGTT, and for exposure response modeling, the insulin AUC in response to the ivGTT is used as the primary endpoint.

An $E_{max}$ model is used to compare the exposure response profiles for Example 1 to semaglutide. In experiments performed essentially as described for this assay, exposure is essentially the same for Example 1 and semaglutide for the dose levels that had drug levels above the limit of quantitation of the assay. Both data sets are fit simultaneously and $E_0$ and $E_{max}$ values are constrained to be the same for both compounds. Only $ED_{50}$ values are fit separately for the compounds. $ED_{50}$ value for semaglutide is estimated as 0.6+/−0.2 nmol/kg. Potency of Example 1 is estimated as a relative potency to semaglutide, and is 1.7+/−0.6 times the potency of semaglutide. Adjusting for CL/F (apparent clearance) differences between the two molecules in monkeys and also for the difference in molecular weight, the projected mean human equivalent dose to 1 mg semaglutide is approximately 1.3 mg/week for Example 1.

Type 2 Diabetes

Rat in vivo insulin secretion following intravenous glucose (IVGTT)

Male Wistar rats (Harlan Labs, Indianapolis, Ind.) are randomized by body weight and dosed 1.5 ml/kg s.c. 16 hour prior to glucose administration and then fasted. Doses are vehicle, 0.1, 0.3, 1, 3 and 10 nmol/kg. Animals are weighed, and then anesthetized with sodium pentobarbital (Nembutal Sodium solution; Ovation Pharmaceuticals) dosed i.p. (65 mg/kg, 30 mg/ml). A time zero blood sample is collected into EDTA tubes after which glucose is administered (0.5 mg/kg, 5 ml/kg). Blood samples are collected at 2, 4, 6, 10, 20, and 30 minutes post glucose. Plasma glucose levels are determined using a Hitachi analyzer (Roche) and plasma insulin is measured by the MSD insulin assay (Meso Scale, Gaithersburg, Md.).

As shown in Table 7, certain compounds of the present invention dose-dependently enhance insulin secretion following i.v. injection of glucose. The $ED_{50}$ for insulin and the maximal increases in insulin secretion (measured as area under the insulin curve) are given in Table 7.

TABLE 7

Enhancement of insulin secretion in the rat IVGTT assay

| Compound | $ED_{50}$ (nmol/kg) | % max increase of insulin AUC |
|---|---|---|
| Example 3 | 1.00 | 314 +/− 38% |
| Example 3 | 1.42 | 219 +/− 19% |
| Example 6 | 2.58 | 289 +/− 4% |
| Example 7 | 4.33 | 335 +/− 35% |
| Example 7 | 1.10 | 278 +/− 26% |
| Example 8 | 6.13 | 324 +/− 30% |
| semaglutide | 0.70 | 231 +/− 13% |
| Example 2 | 1.62 | 233 +/− 19% |
| Example 1 | 0.87 | 298 +/− 17% |
| Example 5 | 1.02 | 349 +/− 39% |

Effect on Weight Loss, Body Composition and Hepatic Steatosis in Diet-Induced Obese (DIO) Mice The effects on weight loss, body composition and hepatic steatosis in DIO mice for compounds of the present invention are evaluated in C57/BL6 DIO mice. These animals, although not diabetic, display insulin resistance, dyslipidemia, and hepatic steatosis, which are all characteristics of metabolic syndrome, after being placed on a high fat (60% Kcal from fat) diet for 12 weeks.

In this study, 23-24 week old male diet-induced obese (DIO) C57/B16 male mice are used, with each weighing 41-49 g and having an initial fat mass ranging from 10.5-17.5 g. Animals are individually housed in a temperature-controlled (24° C.) facility with a 12 hour light/dark cycle (lights on 22:00), and free access to food and water. After 2 weeks acclimation to the facility, the mice are randomized to 5 treatment groups (n=5/group) based on body weight so each group has similar starting mean body weight.

Vehicle control, compounds of the present invention (with dose ranging from 10 to 100 nmol/kg), or a long-acting GLP1 analogue semaglutide (30 nmol/kg), dissolved in vehicle (20 mM Citrate Buffer at pH 7.0), are administered by SC injection to ad libitum fed DIO mice 30-90 minutes prior to the onset of the dark cycle every three days for 15 days. SC injections are made on Day 1, 4, 7, 10, and 13. Daily body weight and food intake are measured throughout the study. Absolute changes in body weight are calculated by subtracting the body weight of the same animal prior to the first injection of compound. On days 0 and 14, total fat mass is measured by nuclear magnetic resonance (NMR) using an Echo Medical System (Houston, Tex.) instrument.

On Day 15, blood glucose is measured with Accu-Chek glucometer (Roche) from tail vein blood and then animals may be sacrificed and livers removed and frozen. Liver triglycerides, determined from homogenates of livers collected at sacrifice, and plasma cholesterol are measured on a Hitachi Modular P clinical analyzer. Statistical comparisons between groups are done using one-way ANOVA followed by Dunnett's multiple comparison test. The $ED_{50}$ for weight loss lowering is determined in GraphPad Prism using the non-linear fit tool.

In experiments performed essentially as described in this assay, certain compounds of the present invention reduced body weight and fat mass in a dose-dependent manner (Table 8-13), and compared to semaglutide, may be 3-5× more efficacious in lowering body weight. The $ED_{50}$ of Example 1 in percent body weight loss is 5.422 nmol/kg (95% Confidence interval levels [nmol/kg]=2.2 to 13.6). Reduced body weight is found to be primarily due to reduction in fat mass.

TABLE 8

Percent body weight or fat mass change in DIO mice.

| Treatment | Dose (nmol/kg) | % Change from starting body weight | % Change from starting fat mass |
|---|---|---|---|
| Control | 0 | −3.14 ± 0.88 | −4.84 ± 1.79 |
| Semaglutide | 10 | −12.36 ± 1.00**** | −18.21 ± 2.24** |
| Semaglutide | 30 | −14.20 ± 1.01**** | −21.90 ± 2.07*** |
| Semaglutide | 100 | −19.30 ± 1.38**** | −33.51 ± 3.30*** |
| Example 3 | 10 | −13.38 ± 0.88**** | −20.76 ± 2.42*** |
| Example 3 | 30 | −18.13 ± 1.44**** | −30.90 ± 2.06**** |

TABLE 8-continued

Percent body weight or fat mass change in DIO mice.

| Treatment | Dose (nmol/kg) | % Change from starting body weight | % Change from starting fat mass |
|---|---|---|---|
| Example 3 | 100 | −25.84 ± 1.93**** | −45.92 ± 2.15**** |
| Example 6 | 10 | −15.31 ± 1.25**** | −24.75 ± 1.89**** |
| Example 6 | 30 | −21.62 ± 0.92**** | −36.30 ± 2.47**** |
| Example 6 | 100 | −33.95 ± 1.93**** | −64.64 ± 4.04**** |

**$p < 0.01$,
***$p < 0.001$,
****$p < 0.0001$ from control group (One-Way ANOVA, Dunnett's).
The results are expressed as Mean ± SEM of 5 mice per group.

TABLE 9

Percent body weight or fat mass change in DIO mice.

| Treatment | Dose (nmol/kg) | % Change from starting body weight | % Change from starting fat mass |
|---|---|---|---|
| Control | 0 | −0.74 ± 1.49 | 3.04 ± 3.65 |
| Semaglutide | 30 | −17.03 ± 0.98**** | −35.94 ± 4.09**** |
| Example 2 | 10 | −23.27 ± 1.72**** | −49.89 ± 5.62**** |
| Example 2 | 30 | 33.07 ± 1.65**** | −72.80 ± 4.04**** |
| Example 2 | 100 | −34.66 ± 1.80**** | −76.20 ± 3.78**** |
| Example 5 | 10 | −23.42 ± 1.43**** | −51.28 ± 1.89**** |
| Example 5 | 30 | −26.84 ± 3.14**** | −62.77 ± 5.49**** |
| Example 5 | 100 | −37.86 ± 2.25**** | −81.08 ± 1.68**** |
| Example 1 | 10 | −25.18 ± 1.82**** | −50.98 ± 2.87**** |
| Example 1 | 30 | −26.58 ± 2.49**** | −59.98 ± 6.60**** |
| Example 1 | 100 | −38.14 ± 1.67**** | −79.79 ± 3.10**** |

****$p < 0.0001$ from control group (One-Way ANOVA, Dunnett's).
The results are expressed as Mean ± SEM of 5 mice per group.

TABLE 10

Percent body weight or fat mass change in DIO mice.

| Treatment | Dose (nmol/kg) | % Change from starting body weight | % Change from starting fat mass |
|---|---|---|---|
| Control | 0 | −2.43 ± 2.06 | −1.49 ± 3.69 |
| Example 6 | 10 | −17.54 ± 1.17**** | −34.30 ± 1.20**** |
| Example 6 | 30 | −19.52 ± 1.18**** | −39.52 ± 3.18**** |
| Example 6 | 100 | −29.36 ± 2.62**** | −56.66 ± 4.96**** |
| Example 7 | 10 | −15.08 ± 1.22**** | −26.46 ± 2.31*** |
| Example 7 | 30 | −20.70 ± 1.95**** | −43.49 ± 5.47**** |
| Example 7 | 100 | −24.36 ± 2.06**** | −49.92 ± 3.40**** |
| Example 8 | 10 | −17.13 ± 0.81**** | −34.20 ± 1.62**** |
| Example 8 | 30 | −25.27 ± 0.70**** | −54.24 ± 2.35**** |
| Example 8 | 100 | −29.91 ± 2.03**** | −65.23 ± 6.69**** |

****$p < 0.001$ from control group (One-Way ANOVA, Dunnett's).
The results are expressed as Mean ± SEM of 5 mice per group.

TABLE 11

Blood glucose, plasma cholesterol and plasma triglycerides in DIO mice.

| Treatment | Dose (nmol/kg) | Blood Glucose (mg/dl) | Plasma Cholesterol (mg/dl) | Plasma Triglycerides (mg/dl) |
|---|---|---|---|---|
| Control | 0 | 141.6 ± 5.59 | 303.2 ± 13.97 | 54.2 ± 11.14 |
| Semaglutide | 10 | 147.6 ± 6.13 | 226.8 ± 13.86** | 27.36 ± 3.56* |
| Semaglutide | 30 | 146.8 ± 8.43 | 229.8 ± 10.96** | 27.9 ± 6.01* |
| Semaglutide | 100 | 134.3 ± 9.22 | 218.4 ± 18.70** | 36.46 ± 5.34 |
| Example 3 | 10 | 109.5 ± 2.35*** | 213.2 ± 15.54*** | 30.38 ± 8.23 |
| Example 3 | 30 | 107.6 ± 1.32*** | 177.4 ± 16.58**** | 21.32 ± 2.48** |
| Example 3 | 100 | 102.00 ± 0.50**** | 194.00 ± 14.40*** | 20.55 ± 4.60** |
| Example 6 | 10 | 105.8 ± 2.10*** | 198.4 ± 6.76**** | 20.78 ± 4.40** |
| Example 6 | 30 | 100.1 ± 3.29**** | 186.4 ± 17.04**** | 26.12 ± 6.85* |

TABLE 11-continued

Blood glucose, plasma cholesterol and plasma triglycerides in DIO mice.

| Treatment | Dose (nmol/kg) | Blood Glucose (mg/dl) | Plasma Cholesterol (mg/dl) | Plasma Triglycerides (mg/dl) |
|---|---|---|---|---|
| Example 6 | 100 | 103.6 ± 3.20**** | 151.4 ± 14.32**** | 17.26 ± 1.67*** |

*p < 0.05,
**p < 0.01,
***p < 0.001,
****p < 0.0001 from control group (One-Way ANOVA, Dunnett's).
The results are expressed as Mean ± SEM of 5 mice per group.

TABLE 12

Blood glucose, plasma cholesterol and liver triglycerides in DIO mice.

| Treatment | Dose (nmol/kg) | Blood Glucose (mg/dl) | Plasma Cholesterol (mg/dl) | Liver Triglycerides (mg/g tissue) |
|---|---|---|---|---|
| Control | 0 | 144.30 ± 8.16 | 233.6 ± 12.99 | 206.65 ± 29.47 |
| Semaglutide | 30 | 136.3 ± 3.81 | 161.0 ± 13.92*** | 67.63 ± 23.40**** |
| Example 2 | 10 | 110.8 ± 3.87** | 121.8 ± 13.64**** | 60.77 ± 13.24**** |
| Example 2 | 30 | 110.8 ± 3.20** | 114.00 ± 9.70**** | 65.78 ± 17.07**** |
| Example 2 | 100 | 113.2 ± 4.86** | 109.4 ± 8.83**** | 56.74 ± 17.76**** |
| Example 5 | 10 | 111.00 ± 6.56** | 126.6 ± 9.67**** | 48.30 ± 8.14**** |
| Example 5 | 30 | 104.5 ± 5.30*** | 108.2 ± 13.84**** | 39.60 ± 4.71**** |
| Example 5 | 100 | 105.3 ± 6.16*** | 108.6 ± 4.83**** | 67.96 ± 13.53**** |
| Example 1 | 10 | 102.3 ± 5.59**** | 120.6 ± 8.55**** | 60.74 ± 5.33**** |
| Example 1 | 30 | 110.7 ± 5.85** | 118.2 ± 10.11**** | 45.24 ± 5.87**** |
| Example 1 | 100 | 106.7 ± 7.33** | 107.6 ± 10.43**** | 66.98 ± 17.29**** |

*p < 0.05,
**p < 0.01,
***p < 0.001,
****p < 0.0001 from control group (One-Way ANOVA, Dunnett's).
The results are expressed as Mean ± SEM of 5 mice per group.

TABLE 13

Blood glucose and plasma cholesterol in DIO mice.

| Treatment | Dose (nmol/kg) | Blood Glucose (mg/dl) | Plasma Cholesterol (mg/dl) |
|---|---|---|---|
| Control | 0 | 152.4 ± 3.63 | 243.6 ± 13.12 |
| Example 6 | 10 | 121.4 ± 2.74*** | 167.8 ± 15.59**** |
| Example 6 | 30 | 121.9 ± 6.65** | 159.8 ± 9.99**** |
| Example 6 | 100 | 116.1 ± 4.67**** | 144.2 ± 7.12**** |
| Example 7 | 10 | 113.6 ± 4.16**** | 161.8 ± 6.2**** |
| Example 7 | 30 | 114.7 ± 4.70**** | 153.6 ± 13.47**** |
| Example 7 | 100 | 114 ± 2.36**** | 145.4 ± 9.48**** |
| Example 8 | 10 | 114.7 ± 4.61**** | 158.8 ± 7.57**** |
| Example 8 | 30 | 117.1 ± 8.26*** | 139.4 ± 6.83**** |
| Example 8 | 100 | 125.4 ± 6.30** | 127.8 ± 6.34**** |

*p < 0.05,
**p < 0.01,
***p < 0.001,
****p < 0.0001 from control group (One-Way ANOVA, Dunnett's).
The results are expressed as Mean ± SEM of 5 mice per group.

The Effect on Energy Metabolism in DIO Mice

The effects on energy metabolism in DIO mice for compounds of the present invention are evaluated in 26 week old C57/B16 DIO male mice, weighing 43-50 g. Mice are individually housed in a temperature-controlled (24° C.) facility with a 12 hour light/dark cycle (lights on 22:00), and with free access to food TD95217 (Teklad) and water. After 2 weeks acclimation to the facility, mice are randomized to treatment groups (n=6/group) based on body weight so each group has similar starting mean body weight. Animals are placed in a PhenoMaster/LabMaster calorimeter (TSE Systems, Chesterfield, Mo.) for 3 days of acclimation. Vehicle control (20 mM citrate buffer at pH 7.0, 10 ml/kg), compounds of the present invention, or a long-acting GLP1 analogue, semaglutide, (30 nmol/kg) are subcutaneously administered to ad libitum fed DIO mice 30-90 minutes prior to the onset of the dark cycle every three days for 22 days. Heat and respiratory quotient (RER) are measured by indirect calorimetry as described using an open-circuit calorimetry system. RER is the ratio of the volume of $CO_2$ produced ($Vco_2$) to the volume of $O_2$ consumed ($Vo_2$). Heat is calculated with full body weight considered:

$$VO2 = FlowML*(V1+V2)/N2Ref*Animal\ weight*100$$

$$VCO2 = FlowML*dCO2/Animal\ weight*100$$

$$Heat = (CVO2*VO2+CVCO2*VCO2)/1000;\ where$$
$$CVO2 = 3.941;\ CVCO2 = 1.106$$

In experiments performed essentially as described in this assay, mice treated with Example 1 significantly increased their metabolic rate 10 to 15% compared to the control group, starting from week 2, and sustained the effect throughout the treatment period. Semaglutide, however, had no effect on metabolic rate. The increase in metabolic rate for Example 1 partially accounts for the additional weight loss observed with Example 1 treatment in comparison with semaglutide treatment.

The Effect on Gastric Emptying in DIO Mice

The effects on gastric emptying in DIO mice for compounds of the present invention are evaluated in 23 week old diet-induced obese (DIO) male mice (Harlan). The mice are fasted for 16-17 hours. During the start of fasting period the mice are dosed subcutaneously with vehicle control (20 mM citrate buffer at pH 7.0); escalating doses of compounds of the present invention (3, 10, 30 and 100 nmol/kg), or a long-acting GLP1 analogue, semaglutide, (30 nmol/kg). The next day, mice are administered 0.5 ml (0.5 gram) of freshly prepared semi-liquid diet (2 minutes apart) by oral gavage. Water is removed at this time to prevent dilution of administered diet. Two hours after diet administration, mice are euthanized two minutes apart by $CO_2$ gas. The stomach is removed while clamped at both cardiac and pyloric openings, then clamps removed and the full stomach weighed in a weigh boat. The stomach is then incised and contents removed. The stomach is washed and dried and re-weighed to assess food contents in stomach. The % gastric emptying equals 100×(1−(food remaining in stomach/food orally administered)).

In experiments performed essentially as described in this assay, Example 1 slowed the gastric emptying rate of the semi-liquid diet in a dose dependent manner. The maximum inhibition of gastric emptying was observed at a dose of 10 nmol/kg+/−dose (Table 14).

TABLE 14

Gastric emptying of a semi-liquid diet in lean C57/BL6 DIO mice.

| Treatment | Dose (nmol/kg) | Percent Gastric Emptying (Mean ± SEM) |
|---|---|---|
| Vehicle (n = 5) | 0 | 69.50 +/− 6.60 |
| Semaglutide (n = 5) | 30 | 30.56 +/− 7.53** |
| Example 1 (n = 4) | 3 | 49.11 +/− 8.52 |
| Example 1 (n = 5) | 10 | 9.76 +/− 7.69**** |
| Example 1 (n = 5) | 30 | 26.53 +/− 8.14** |
| Example 1 (n = 5) | 100 | 18.45 +/− 6.87*** |

Statistical comparisons between groups are done by using one-way ANOVA followed by Dunnett's multiple comparison test.
*p <0.05,
**p <0.01,
***p <0.001,
****p <0.0001 from control group.
The results are expressed as mean +/− SEM of 4-5 mice per group.

Plasma Corticosterone Measurements in Sprague Dawley Rats

As suggested in certain published studies, elevated plasma corticosterone levels are an indicator of possible reduced tolerability for GIP and GLP-1 analogues. Plasma corticosterone levels are evaluated using Sprague Dawley Rats (Harlan, Indianapolis), weighing approximately 220 g and acclimated for at least 72 hours before handling. The rats are then dosed with vehicle (20 mM citrate buffer, pH 7), semaglutide (10 nmol/kg), or compounds of the present invention at 3, 10 or 30 nmol/kg s.c. with 8 rats per dose group. The rats are decapitated 16 hours later. Blood is collected into EDTA tubes on ice, then centrifuged 5 minutes at 8000 RPM in a Eppendorf 5402 tabletop centrifuge. Plasma is stored at −80° C. until analysis.

For corticosterone analysis, corticosterone standards (Sigma, 27840) are prepared by serial dilutions in HPLC-grade methanol, $H_2O$ and the addition of 5% charcoal stripped rat serum (Bioreclamation, RATSRM-STRPD-HEV). Rat plasma samples are diluted with PBS, precipitated with cold methanol, incubated for 20 minutes at −20° C., and then centrifuged at 14,000 RPM with an Eppendorf 5417R at 4° C. Supernatants are extracted, evaporated under a stream of $N_2$ gas, and reconstituted in $MeOH/H_2O$ (1:1) solution. Samples are analyzed on the LC/MS equipped with a XSelect CSH C18 3.5 μm HPLC column (2.1 mm×30 mm) (Waters #186005254).

In experiments performed essentially as described for this assay, Example 1 demonstrated no increase in plasma corticosterone levels at any of the doses tested while semaglutide had an approximately 4× increase over control.

TABLE 15

Plasma corticosterone analysis in Sprague Dawley Rats

| | Corticosterone (ng/ml) | |
|---|---|---|
| Compound | Mean | SEM |
| Vehicle | 60.78 | 8.41 |
| 10 nmol/kg Semaglutide | 274.57 | 42.06 |
| 3 nmol/kg Example 1 | 52.21 | 19.39 |
| 10 nmol/kg Example 1 | 32.46 | 9.78 |
| 30 nmol/kg Example 1 | 31.35 | 5.86 |

Amino Acid Sequences
(Human GIP)

SEQ ID NO: 1
YAEGTFISDYSIAMDKIHQQDFVNWLLAQKGKKNDWKHNITQ (Human GLP-1)

SEQ ID NO: 2
HAEGTFTSDVSSYLEGQAAKEFIAWLVKGR

SEQ ID NO: 3
YX$_1$EGTFTSDYSIX$_2$LDKIAQKAFVQWLIAGGPSSGAPPPS wherein $X_1$ is Aib; $X_2$ is Aib; K at position 20 is chemically modified through conjugation to the epsilon-amino group of the K side-chain with ([2-(2-Amino-ethoxy)-ethoxy]-acetyl)$_2$-(γGlu)$_1$-CO—(CH$_2$)$_{18}$—CO$_2$H; and the C-terminal amino acid is amidated as a C-terminal primary amide.

SEQ ID NO: 4
YX$_1$EGTFTSDYSIX$_2$LDKIAQKAX$_3$VQWLIAGGPSSGAPPPS wherein $X_1$ is Aib; $X_2$ is Aib; K at position 20 is chemically modified through conjugation to the epsilon-amino group of the K side-chain with ([2-(2-Amino-ethoxy)-ethoxy]-acetyl)$_2$-(γGlu)$_2$-CO—(CH$_2$)$_{18}$—CO$_2$H; $X_3$ is 1-Nal; and the C-terminal amino acid is amidated as a C-terminal primary amide.

SEQ ID NO: 5
YX$_1$EGTFTSDYSIX$_2$LDKIAQKAFVQWLIAGGPSSGAPPPS wherein $X_1$ is Aib; $X_2$ is Aib; K at position 20 is chemically modified through conjugation to the epsilon-amino group of the K side-chain with ([2-(2-Amino-ethoxy)-ethoxy]-acetyl)$_2$-(γGlu)$_1$-CO—(CH$_2$)$_{16}$—CO$_2$H; and the C-terminal amino acid is amidated as a C-terminal primary amide.

SEQ ID NO: 6
YX$_1$EGTFTSDYSIX$_2$LDKIAQKAFVQWLIAGGPSSGAPPPS wherein $X_1$ is Aib; $X_2$ is Aib; K at position 20 is chemically modified through conjugation to the epsilon-amino group of the K side-chain with ([2-(2-Amino-ethoxy)-ethoxy]-acetyl)$_2$-(γGlu)$_2$-CO—(CH$_2$)$_{16}$—CO$_2$H; and the C-terminal amino acid is amidated as a C-terminal primary amide.

SEQ ID NO: 7
YX₁EGTFTSDYSIX₂LDKIAQKAFVQWLIAGGPSSGAPPPS wherein $X_1$ is Aib; $X_2$ is Aib; K at position 20 is chemically modified through conjugation to the epsilon-amino group of the K side-chain with ([2-(2-Amino-ethoxy)-ethoxy]-acetyl)$_2$-($\gamma$Glu)$_2$-CO—(CH$_2$)$_{18}$—CO$_2$H; and the C-terminal amino acid is amidated as a C-terminal primary amide.

SEQ ID NO: 8
YX₁EGTFTSDYSIX₂LDKIAQKAX₃VQWLIAGGPSSGAPPPS wherein $X_1$ is Aib; $X_2$ is Aib; K at position 20 is chemically modified through conjugation to the epsilon-amino group of the K side-chain with ([2-(2-Amino-ethoxy)-ethoxy]-acetyl)$_2$-($\gamma$Glu)$_1$-CO—(CH$_2$)$_{16}$—CO$_2$H; $X_3$ is 1-Nal; and the C— terminal amino acid is amidated as a C-terminal primary amide.

SEQ ID NO: 9
YX₁EGTFTSDYSIX₂LDKIAQKAX₃VQWLIAGGPSSGAPPPS wherein $X_1$ is Aib; $X_2$ is Aib; K at position 20 is chemically modified through conjugation to the epsilon-amino group of the K side-chain with ([2-(2-Amino-ethoxy)-ethoxy]-acetyl)$_2$-($\gamma$Glu)$_2$-CO—(CH$_2$)$_{16}$—CO$_2$H; $X_3$ is 1-Nal; and the C-terminal amino acid is amidated as a C-terminal primary amide.

SEQ ID NO: 10
YX₁EGTFTSDYSIX₂LDKIAQKAX₃VQWLIAGGPSSGAPPPS wherein $X_1$ is Aib; $X_2$ is Aib; K at position 20 is chemically modified through conjugation to the epsilon-amino group of the K side-chain with ([2-(2-Amino-ethoxy)-ethoxy]-acetyl)$_2$-($\gamma$Glu)$_1$-CO—(CH$_2$)$_{18}$—CO$_2$H; $X_3$ is 1-Nal; and the C-terminal amino acid is amidated as a C-terminal primary amide.

SEQ ID NO: 11
YX₁EGTFTSDYSIX₂LDKIAQKAX₃VQWLIAGGPSSGAPPPS wherein $X_1$ is Aib; $X_2$ is Aib; K at position 20 is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H wherein a is 1 to 2 and b is 10 to 20; $X_3$ is Phe or 1-Nal; and the C-terminal amino acid is optionally amidated as a C-terminal primary amide.

SEQUENCE LISTING

```
<160> NUMBER OF SEQ ID NOS: 11

<210> SEQ ID NO 1
<211> LENGTH: 42
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 30
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
```

```
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (13)..(13)
<223> OTHER INFORMATION: Xaa at position 13 is nonnaturally occurring
      amino acid 2-Aminoisobutyric Acid
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified
      through conjugation to the epsilon-amino group of the K side-chain
      with ([2-(2-Amino-ethoxy)-ethoxy]-acetyl)2-(gamma-Glu)1-CO-
      (CH2)18-CO2H
<220> FEATURE:
<221> NAME/KEY: MOD_RES
<222> LOCATION: (39)..(39)
<223> OTHER INFORMATION: Ser at position 39 is amidated as a C-terminal
      primary amide

<400> SEQUENCE: 3

Tyr Xaa Glu Gly Thr Phe Thr Ser Asp Tyr Ser Ile Xaa Leu Asp Lys
1               5                   10                  15

Ile Ala Gln Lys Ala Phe Val Gln Trp Leu Ile Ala Gly Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (13)..(13)
<223> OTHER INFORMATION: Xaa at position 13 is nonnaturally occurring
      amino acid 2-Aminoisobutyric Acid
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified
      through conjugation to the epsilon-amino group of the K side-chain
      with ([2-(2-Amino-ethoxy)-ethoxy]-acetyl)2-(gamma-Glu)2-CO-
      (CH2)18-CO2H
<220> FEATURE:
<221> NAME/KEY: MISC_FEATURE
<222> LOCATION: (22)..(22)
<223> OTHER INFORMATION: Xaa at position 22 is 1-Nal
<220> FEATURE:
<221> NAME/KEY: MOD_RES
<222> LOCATION: (39)..(39)
<223> OTHER INFORMATION: Ser at position 39 is amidated as a C-terminal
      primary amide

<400> SEQUENCE: 4
```

Tyr Xaa Glu Gly Thr Phe Thr Ser Asp Tyr Ser Ile Xaa Leu Asp Lys
1               5                   10                  15

Ile Ala Gln Lys Ala Xaa Val Gln Trp Leu Ile Ala Gly Gly Pro Ser
                20                  25                  30

Ser Gly Ala Pro Pro Pro Ser
            35

<210> SEQ ID NO 5
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (13)..(13)
<223> OTHER INFORMATION: Xaa at position 13 is nonnaturally occurring
      amino acid 2-Aminoisobutyric Acid
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified
      through conjugation to the epsilon-amino group of the K side-chain
      with ([2-(2-Amino-ethoxy)-ethoxy]-acetyl)2-(gamma-Glu)1-CO-
      (CH2)16-CO2H
<220> FEATURE:
<221> NAME/KEY: MOD_RES
<222> LOCATION: (39)..(39)
<223> OTHER INFORMATION: Ser at position 39 is amidated as a C-terminal
      primary amide

<400> SEQUENCE: 5

Tyr Xaa Glu Gly Thr Phe Thr Ser Asp Tyr Ser Ile Xaa Leu Asp Lys
1               5                   10                  15

Ile Ala Gln Lys Ala Phe Val Gln Trp Leu Ile Ala Gly Gly Pro Ser
                20                  25                  30

Ser Gly Ala Pro Pro Pro Ser
            35

<210> SEQ ID NO 6
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (13)..(13)
<223> OTHER INFORMATION: Xaa at position 13 is nonnaturally occurring

```
      amino acid 2-Aminoisobutyric Acid
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified
      through conjugation to the epsilon-amino group of the K side-chain
      with ([2-(2-Amino-ethoxy)-ethoxy]-acetyl)2-(gamma-Glu)2-CO-
      (CH2)16-CO2H
<220> FEATURE:
<221> NAME/KEY: MOD_RES
<222> LOCATION: (39)..(39)
<223> OTHER INFORMATION: Ser at position 39 is amidated as a C-terminal
      primary amide

<400> SEQUENCE: 6

Tyr Xaa Glu Gly Thr Phe Thr Ser Asp Tyr Ser Ile Xaa Leu Asp Lys
1               5                   10                  15

Ile Ala Gln Lys Ala Phe Val Gln Trp Leu Ile Ala Gly Gly Pro Ser
            20                  25                  30

Ser Gly Ala Pro Pro Pro Ser
        35

<210> SEQ ID NO 7
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (13)..(13)
<223> OTHER INFORMATION: Xaa at position 13 is nonnaturally occurring
      amino acid 2-Aminoisobutyric Acid
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified
      through conjugation to the epsilon-amino group of the K side-chain
      with ([2-(2-Amino-ethoxy)-ethoxy]-acetyl)2-(gamma-Glu)2-CO-
      (CH2)18-CO2H
<220> FEATURE:
<221> NAME/KEY: MOD_RES
<222> LOCATION: (39)..(39)
<223> OTHER INFORMATION: Ser at position 39 is amidated as a C-terminal
      primary amide

<400> SEQUENCE: 7

Tyr Xaa Glu Gly Thr Phe Thr Ser Asp Tyr Ser Ile Xaa Leu Asp Lys
1               5                   10                  15

Ile Ala Gln Lys Ala Phe Val Gln Trp Leu Ile Ala Gly Gly Pro Ser
            20                  25                  30

Ser Gly Ala Pro Pro Pro Ser
        35
```

```
<210> SEQ ID NO 8
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (13)..(13)
<223> OTHER INFORMATION: Xaa at position 13 is nonnaturally occurring
      amino acid 2-Aminoisobutyric Acid
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified
      through conjugation to the epsilon-amino group of the K side-chain
      with ([2-(2-Amino-ethoxy)-ethoxy]-acetyl)2-(gamma-Glu)1-CO-
      (CH2)16-CO2H
<220> FEATURE:
<221> NAME/KEY: MISC_FEATURE
<222> LOCATION: (22)..(22)
<223> OTHER INFORMATION: Xaa at position 22 is 1-Nal
<220> FEATURE:
<221> NAME/KEY: MOD_RES
<222> LOCATION: (39)..(39)
<223> OTHER INFORMATION: Ser at position 39 is amidated as a C-terminal
      primary amide

<400> SEQUENCE: 8

Tyr Xaa Glu Gly Thr Phe Thr Ser Asp Tyr Ser Ile Xaa Leu Asp Lys
1               5                   10                  15

Ile Ala Gln Lys Ala Xaa Val Gln Trp Leu Ile Ala Gly Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (13)..(13)
<223> OTHER INFORMATION: Xaa at position 13 is nonnaturally occurring
      amino acid 2-Aminoisobutyric Acid
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
```

```
<222> LOCATION: (20)..(20)
<223> OTHER INFORMATION: Lys at position 20 is chemically modified
      through conjugation to the epsilon-amino group of the K side-chain
      with ([2-(2-Amino-ethoxy)-ethoxy]-acetyl)2-(gamma-Glu)2-CO-
      (CH2)16-CO2H
<220> FEATURE:
<221> NAME/KEY: MISC_FEATURE
<222> LOCATION: (22)..(22)
<223> OTHER INFORMATION: Xaa at position 22 is 1-Nal
<220> FEATURE:
<221> NAME/KEY: MOD_RES
<222> LOCATION: (39)..(39)
<223> OTHER INFORMATION: Ser at position 39 is amidated as a C-terminal
      primary amide

<400> SEQUENCE: 9

Tyr Xaa Glu Gly Thr Phe Thr Ser Asp Tyr Ser Ile Xaa Leu Asp Lys
1               5                   10                  15

Ile Ala Gln Lys Ala Xaa Val Gln Trp Leu Ile Ala Gly Gly Pro Ser
            20                  25                  30

Ser Gly Ala Pro Pro Pro Ser
        35

<210> SEQ ID NO 10
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (13)..(13)
<223> OTHER INFORMATION: Xaa at position 13 is nonnaturally occurring
      amino acid 2-Aminoisobutyric Acid
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified
      through conjugation to the epsilon-amino group of the K side-chain
      with ([2-(2-Amino-ethoxy)-ethoxy]-acetyl)2-(gamma-Glu)1-CO-
      (CH2)18-CO2H
<220> FEATURE:
<221> NAME/KEY: MISC_FEATURE
<222> LOCATION: (22)..(22)
<223> OTHER INFORMATION: Xaa at position 22 is 1-Nal
<220> FEATURE:
<221> NAME/KEY: MOD_RES
<222> LOCATION: (39)..(39)
<223> OTHER INFORMATION: Ser at position 39 is amidated as a C-terminal
      primary amide

<400> SEQUENCE: 10

Tyr Xaa Glu Gly Thr Phe Thr Ser Asp Tyr Ser Ile Xaa Leu Asp Lys
1               5                   10                  15

Ile Ala Gln Lys Ala Xaa Val Gln Trp Leu Ile Ala Gly Gly Pro Ser
            20                  25                  30

Ser Gly Ala Pro Pro Pro Ser
        35
```

```
<210> SEQ ID NO 11
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (13)..(13)
<223> OTHER INFORMATION: Xaa at position 13 is nonnaturally occurring
      amino acid 2-Aminoisobutyric Acid
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified
      through conjugation to the epsilon-amino group of the K side-chain
      with ([2-(2-Amino-ethoxy)-ethoxy]-acetyl)2-(gamma-Glu)a-CO-
      (CH2)b-CO2H wherein a is 1 to 2 and b is 10 to 20
<220> FEATURE:
<221> NAME/KEY: MISC_FEATURE
<222> LOCATION: (22)..(22)
<223> OTHER INFORMATION: Xaa at position 22 is either Phe or 1-Nal
<220> FEATURE:
<221> NAME/KEY: MOD_RES
<222> LOCATION: (39)..(39)
<223> OTHER INFORMATION: Ser at position 39 is optionally amidated as a
      C-terminal primary amide

<400> SEQUENCE: 11

Tyr Xaa Glu Gly Thr Phe Thr Ser Asp Tyr Ser Ile Xaa Leu Asp Lys
1               5                   10                  15

Ile Ala Gln Lys Ala Xaa Val Gln Trp Leu Ile Ala Gly Gly Pro Ser
            20                  25                  30

Ser Gly Ala Pro Pro Pro Ser
            35
```

We claim:

1. A compound of Formula:

$YX_1EGTFTSDYSIX_2LDKIAQKAX_3VQWLIAGGPSSGAPPPS;$ wherein $X_1$ is Aib;

$X_2$ is Aib;

K at position 20 is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H wherein a is 1 to 2 and b is 10 to 20;

$X_3$ is Phe or 1-Nal;

and the C-terminal amino acid is optionally amidated as a C-terminal primary amide (SEQ ID NO: 11), or a pharmaceutically acceptable salt thereof.

2. The compound of claim 1, wherein $X_3$ is Phe.

3. The compound of claim 1, wherein $X_3$ is 1-Nal.

4. The compound of claim 2, wherein b is 14 to 18.

5. The compound of claim 4, wherein b is 16 to 18.

6. The compound of claim 5, wherein b is 18.

7. The compound of claim 4, wherein a is 1.

8. The compound of claim 4, wherein a is 2.

9. The compound of claim 4, wherein the C-terminal amino acid is amidated as a C-terminal primary amide.

10. The compound of claim 1, wherein $X_1$ is Aib $X_2$ is Aib;

K at position 20 is chemically modified through conjugation to the epsilon-amino group of the K side-chain with ([2-(2-Amino-ethoxy)-ethoxy]-acetyl)$_2$-(γGlu)$_1$-CO—(CH$_2$)$_{18}$—CO$_2$H;

$X_3$ is Phe;

and the C-terminal amino acid is amidated as a C-terminal primary amide (SEQ ID NO: 3), or a pharmaceutically acceptable salt thereof.

11. The compound of claim 1, wherein $X_1$ is Aib $X_2$ is Aib;

K at position 20 is chemically modified through conjugation to the epsilon-amino group of the K side-chain with ([2-(2-Amino-ethoxy)-ethoxy]-acetyl)$_2$-(γGlu)$_2$-CO—(CH$_2$)$_{18}$—CO$_2$H;

X$_3$ is 1-Nal;

and the C-terminal amino acid is amidated as a C-terminal primary amide (SEQ ID NO: 4), or a pharmaceutically acceptable salt thereof.

12. A pharmaceutical composition comprising the compound of claim 10 with a pharmaceutically acceptable carrier, diluent, or excipient.

13. A method of treating type 2 diabetes mellitus, comprising administering to a patient in need thereof, an effective amount of the compound of claim 10.

14. The method of claim 13, further comprising administering simultaneously, separately, or sequentially in combination with an effective amount of one or more agents selected from metformin, thiazolidinediones, sulfonylureas, dipeptidyl peptidase 4 inhibitors, and sodium glucose co-transporters.

15. The compound of claim 1, wherein the Formula is

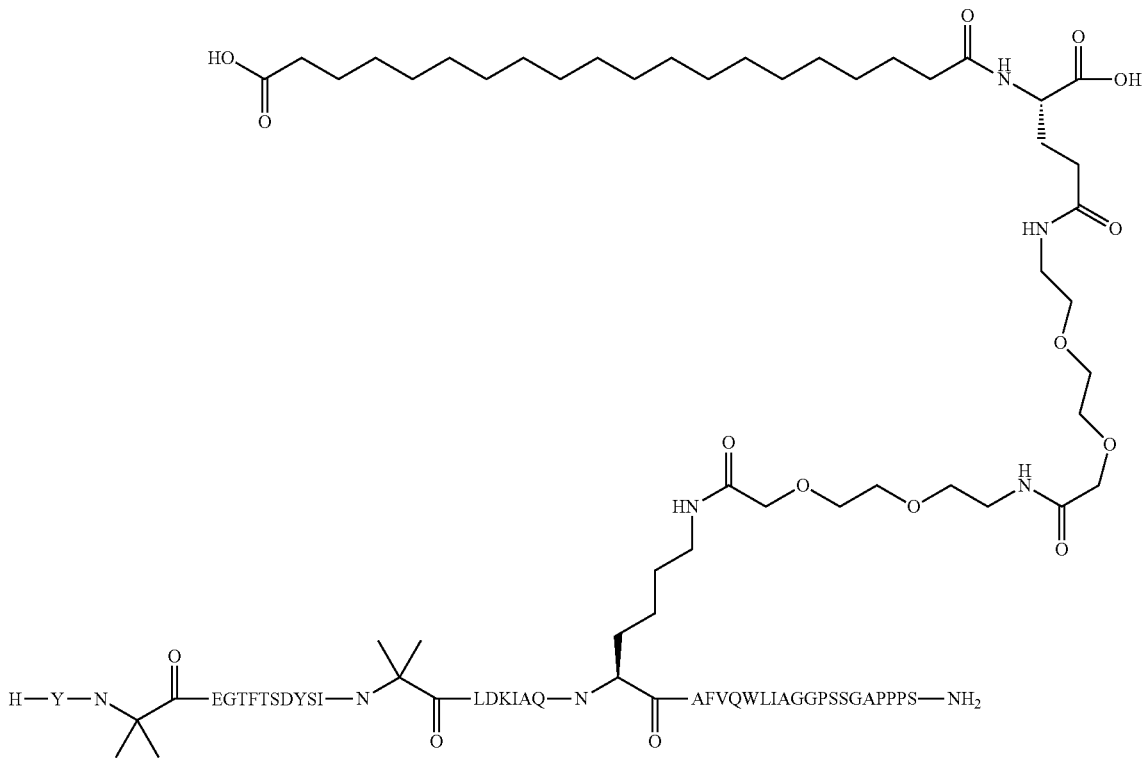

16. A pharmaceutical composition comprising the compound of claim 15 with a pharmaceutically acceptable carrier, diluent, or excipient.

17. A method of treating type 2 diabetes mellitus, comprising administering to a patient in need thereof, an effective amount of the compound of claim 15.

18. The method of claim 17, further comprising administering simultaneously, separately, or sequentially in combination with an effective amount of one or more agents selected from metformin, thiazolidinediones, sulfonylureas, dipeptidyl peptidase 4 inhibitors, and sodium glucose co-transporters.

* * * * *

UNITED STATES PATENT AND TRADEMARK OFFICE
CERTIFICATE OF CORRECTION

| | |
|---|---|
| PATENT NO. | : 9,474,780 B2 |
| APPLICATION NO. | : 14/987791 |
| DATED | : October 25, 2016 |
| INVENTOR(S) | : Jorge Alsina-Fernandez et al. |

It is certified that error appears in the above-identified patent and that said Letters Patent is hereby corrected as shown below:

In the Claims

In Claim 15, after "NH2" insert --.--

Signed and Sealed this
Seventh Day of March, 2017

Michelle K. Lee
*Director of the United States Patent and Trademark Office*